US011786163B2

(12) United States Patent
Garten et al.

(10) Patent No.: US 11,786,163 B2
(45) Date of Patent: Oct. 17, 2023

(54) SYSTEM AND METHOD FOR ASSOCIATING MUSIC WITH BRAIN-STATE DATA

(71) Applicant: INTERAXON INC, Toronto (CA)

(72) Inventors: Ariel Stephanie Garten, Toronto (CA); Christopher Allen Aimone, Toronto (CA); Trevor Coleman, Toronto (CA); Kapil Jay Mishra Vidyarthi, Toronto (CA); Locillo (Lou) Giuseppe Pino, Cambridge (CA); Michael Apollo Chabior, Oakville (CA); Paul Harrison Baranowski, Toronto (CA); Raul Rajiv Rupsingh, Brampton (CA); Madeline Ashby, Toronto (CA); Paul V. Tadich, Toronto (CA); Graeme Daniel Moffat, Toronto (CA); Javier Arturo Moreno Camargo, Toronto (CA)

(73) Assignee: INTERAXON INC., Toronto (CA)

( * ) Notice: Subject to any disclaimer, the term of this patent is extended or adjusted under 35 U.S.C. 154(b) by 1210 days.

(21) Appl. No.: 16/394,563

(22) Filed: Apr. 25, 2019

(65) Prior Publication Data
US 2019/0246936 A1 Aug. 15, 2019

Related U.S. Application Data

(63) Continuation of application No. 14/693,480, filed on Apr. 22, 2015, now Pat. No. 10,321,842.
(Continued)

(51) Int. Cl.
*A61B 5/38* (2021.01)
*A61B 5/316* (2021.01)
(Continued)

(52) U.S. Cl.
CPC ............... *A61B 5/38* (2021.01); *A61B 5/165* (2013.01); *A61B 5/316* (2021.01); *A61B 5/375* (2021.01);
(Continued)

(58) Field of Classification Search
CPC .......... A61B 5/38; A61B 5/165; A61B 5/316; A61B 5/375; A61B 5/486; A61B 5/742;
(Continued)

(56) References Cited

U.S. PATENT DOCUMENTS 4,883,067 A  11/1989  Knispel et al.
5,474,082 A  12/1995  Junker
(Continued)

OTHER PUBLICATIONS

USPTO, Office Action for U.S. Appl. No. 14/693,480 dated Aug. 1, 2018.

*Primary Examiner* — Navin Natnithithadha
(74) *Attorney, Agent, or Firm* — Norton Rose Fulbright Canada LLP

(57) ABSTRACT

A system and method may be provided for associating bio-signal data (e.g. EEG brain scan data) from at least one user with at least one music data item (e.g. song, or piece of music). By associating bio-signal data, or emotions determined therefrom, with music, the system may establish a data store of music associated with emotions. That database may then be leveraged upon determining that a user is feeling a particular emotion through an EEG scan. When a particular emotion is detected in EEG data of a user, the system may then respond based at least partly on the same or similar emotion being associated with one or more music data items in the system. For example, the system may recommend a particular song associated with the same emotion presently being experienced by the user.

19 Claims, 15 Drawing Sheets

Related U.S. Application Data

(60) Provisional application No. 61/982,631, filed on Apr. 22, 2014.

(51) Int. Cl.
    *A61B 5/375*       (2021.01)
    *A61M 21/00*      (2006.01)
    *A61B 5/16*        (2006.01)
    *A61B 5/00*        (2006.01)

(52) U.S. Cl.
    CPC .............. *A61B 5/486* (2013.01); *A61B 5/742* (2013.01); *A61M 21/00* (2013.01); *A61M 2021/0027* (2013.01); *A61M 2205/3375* (2013.01); *A61M 2205/3561* (2013.01); *A61M 2205/3584* (2013.01); *A61M 2205/502* (2013.01); *A61M 2205/52* (2013.01); *A61M 2230/06* (2013.01); *A61M 2230/10* (2013.01); *A61M 2230/42* (2013.01); *A61M 2230/60* (2013.01); *A61M 2230/65* (2013.01)

(58) Field of Classification Search
    CPC .................. A61B 5/163; A61M 21/00; A61M 2021/0027; A61M 2205/3375; A61M 2205/3561; A61M 2205/3584; A61M 2205/502; A61M 2205/52; A61M 2230/06; A61M 2230/10; A61M 2230/42; A61M 2230/60; A61M 2230/65
    See application file for complete search history.

(56) References Cited

U.S. PATENT DOCUMENTS

| | | | |
|---|---|---|---|
| 5,740,812 A | 4/1998 | Cowan | |
| 7,081,579 B2 | 7/2006 | Alcalde et al. | |
| 7,797,272 B2 | 9/2010 | Picker et al. | |
| 8,519,249 B2 | 8/2013 | Alcalde et al. | |
| 8,636,640 B2 | 1/2014 | Chang | |
| 8,684,742 B2* | 4/2014 | Siefert | G06F 3/013 705/7.31 |
| 9,454,646 B2* | 9/2016 | Siefert | G09B 7/073 |
| 9,557,957 B2 | 1/2017 | Guan et al. | |
| 9,983,670 B2 | 5/2018 | Coleman et al. | |
| 10,009,644 B2* | 6/2018 | Aimone | H04N 21/4307 |
| 10,248,195 B2* | 4/2019 | Siefert | G06V 40/70 |
| 10,321,842 B2* | 6/2019 | Garten | A61B 5/375 |
| 10,405,025 B2* | 9/2019 | Aimone | G16Z 99/00 |
| 10,856,032 B2* | 12/2020 | Aimone | A61B 5/165 |
| 11,200,964 B2* | 12/2021 | Siefert | G09B 5/10 |
| 11,259,066 B2* | 2/2022 | Aimone | A61B 5/165 |
| 2003/0060728 A1 | 3/2003 | Mandigo | |
| 2006/0102171 A1 | 5/2006 | Gavish | |
| 2006/0143647 A1 | 6/2006 | Bill | |
| 2010/0004977 A1* | 1/2010 | Marci | H04N 21/44218 705/7.32 |
| 2011/0256520 A1* | 10/2011 | Siefert | G06V 40/70 434/322 |
| 2012/0290950 A1* | 11/2012 | Rapaport | H04N 21/8358 715/753 |
| 2014/0214335 A1* | 7/2014 | Siefert | A61B 5/0205 702/19 |
| 2014/0223462 A1* | 8/2014 | Aimone | G16H 40/67 725/10 |
| 2014/0246502 A1 | 9/2014 | Proud et al. | |
| 2014/0307878 A1* | 10/2014 | Osborne | G10H 1/0008 381/56 |
| 2014/0309484 A1 | 10/2014 | Chang | |
| 2015/0112409 A1 | 4/2015 | Hagedorn | |
| 2015/0297109 A1* | 10/2015 | Garten | A61B 5/316 600/28 |
| 2015/0351655 A1 | 12/2015 | Coleman | |
| 2016/0055420 A1* | 2/2016 | Karanam | A61B 5/7246 700/52 |
| 2016/0220198 A1 | 8/2016 | Proud | |
| 2016/0357256 A1* | 12/2016 | Siefert | A61B 5/0205 |
| 2017/0339484 A1 | 11/2017 | Kim | |

\* cited by examiner

Brain State of Audio Database – Part of the User's profile

| Time | Location (GPS) | Brain State | Audio category |
|---|---|---|---|
| March 12, 2014 1:12:32 | 41° 24' 12.1674", 2° 29' 19" | Anxious | Car Horn |
| March 14, 2014 15:35:21 | 43° 29' 12.14", 2° 10' 26" | Happy | Waves crashing on beach |

| Song | Emotion Before Listening | Emotional State after Listening |
|---|---|---|
| Let It Be | Sad | Hopeful |
| Let It Be | Happy | Inspired |
| ..... | ..... | ..... |

Interface display of Engagement - Energy Space for User Input

SYSTEM AND METHOD FOR ASSOCIATING MUSIC WITH BRAIN-STATE DATA

This application is a continuation of U.S. application Ser. No. 14/693,480, filed Apr. 22, 2015, which claims the benefit of U.S. Provisional Application No. 61/982,631, filed Apr. 22, 2014.

FIELD

Embodiments described herein relate to bio-signal collection methods, and systems that utilize bio-signal data. Embodiments described herein relate more particularly to utilizing bio-signal data to control a computer response.

INTRODUCTION

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns, which may be measured or monitored using an electroencephalogram (EEG). These electrical patterns, or brainwaves, are measurable by devices such as and EEG. Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces (BCI) have been developed that allow users to control devices and computers using brainwave signals.

SUMMARY

In accordance with an aspect of the embodiments described herein, a system is provided with a database that is built of a user's EEG response to specific musical pieces. Combined with other information such as the user's music selections, personality questions, and demographic information, a list of songs can be recommended. The songs the system recommends may be based on the current emotional state of the user and the desired state of the user. In addition users can over-ride the predictions of the system helping improve its prediction algorithms.

In accordance with an aspect of the embodiments described herein, there is provided an intelligent music system. The system may have at least one bio-signal sensor configured to capture bio-signal sensor data from at least one user. The system may have an input receiver configured to receive music data and the bio-signal sensor data, the music data and the bio-signal sensor data being temporally defined such that the music data corresponds temporally to at least a portion of the bio-signal sensor data. The system may have at least one processor configured to provide: a music processor to segment the music data into a plurality of time epochs of music, each epoch of music linked to a time stamp; a sonic feature extractor to, for each epoch of music, extract a set of sonic features; a biological feature extractor to extract, for each epoch of music, a set of biological features from the bio-signal sensor data using the time stamp for the respective epoch of music; a metadata extractor to extract metadata from the music data; a user feature extractor to extract a set of user attributes from the music data and the bio-signal sensor data, the user attributes comprising one or more user actions taken during playback of the music data; a machine learning engine to transform the set of sonic features, the set of biological features, the set of metadata, and the set of user attributes into, for each epoch of music, a set of categories that the respective epoch belongs to using one or more predictive models to predict a user reaction of music; and a music recommendation engine configured to provide at least one music recommendation based on the set of labels or classes.

In some embodiments, the input receiver may be configured to receive a target emotional state and wherein the system further comprises a music controller to interact with the music recommendation engine to provide at least one music recommendation based on the target emotional state.

In some embodiments, the music processor may be configured to identify a selection of songs from the music data and add a temporal history to the selection of songs, the temporal history indicating a date and time a user of the at least one users listened to or otherwise selected songs of the selection of songs and an order of the selection of songs, wherein the predictive models use a temporal model for the temporal history the selection of songs.

In some embodiments, the selection of songs provides at least a portion of the metadata used for the recommendation.

In some embodiments, the at least one processor may be configured to provide the one or more predictive models has a learning mode and an operational mode.

In some embodiments, each of the categories may be nested in a hierarchy of nodes or an ordered list of probabilities of the respective category.

In some embodiments, the system may have a plurality of bio-signal sensors configured to capture bio-signal sensor data from a plurality of users and correlate a portion of the bio-signal sensor data across the plurality of users, the portion being mapped to one or more epochs of music, wherein the machine learning engine transform the portion of the bio-signal sensor data across the plurality of users to a common set of categories for use in music recommendations.

In some embodiments, the system may have a music effect controller to influence user state by playback or recording of music based the at least one music recommendation.

In another aspect, embodiments described herein may provide an intelligent music system. The system may have at least one bio-signal sensor comprising at least one brainwave sensor. The system may have at least one computing device in communication with the least one bio-signal sensor to continuously receive bio-signal data comprising brainwave data of at least one user. The at least one computing device may be configured to: define a profile for the at least one user comprising the brainwave data, and user attributes, the brainwave data linked to a timeline; detect an EEG response as a segment of the brainwave data at a time period on the timeline, the EEG response defining a change in brain state; correlate the time period to music data to compute a segment of music data corresponding to the segment of the brainwave data of the EEG response; identify a selection of music data using the segment of music data and the user attributes; and transmit signals defining a recommendation of a music data item based on the selection of music data.

In some embodiments, at least one computing device is configured to take multiple samples of the brainwave data a different times to detect a plurality of EEG responses and timestamp any detected EEG response.

In some embodiments, the user attributes may have data fields defining music selections, personality data, and demographic data.

In some embodiments, the EEG response defines a current emotional state of the user, and the selection of music data is linked to a desired emotional state relative to the current emotional state.

In some embodiments, the at least one computing device is configured to receive user feedback to reject or accept the recommendation based on the selection of music data, and refine subsequent selections of music data based on the user feedback.

In some embodiments, the at least one computing device configured to identify the selection of music data by identifying users that have similar EEG responses to the detected EEG response.

In some embodiments, the user attributes have data fields defining at least one mental state, and the selection of music data is linked to treatment for the at least one mental state.

In some embodiments, in the computing device may be configured to determine a correspondence between the received brainwave data and historical data available to the system associated with at least one second user; and trigger a user correspondence action based at least partly on the determined correspondence.

In some embodiments, the at least one computing device may be configured to provide at least one digital content item to at least one user at the at least one computing device, determine at least one emotion exhibited by the received brainwave data; and associate the at least one emotion with the at least one digital content item.

In some embodiments, the at least one bio-signal sensors has sensors for receiving data defining physiological measurements of the user.

In some embodiments, the system has cloud data storage connected to the at least one computing device, the cloud data storage storing the profile, the music data and the brainwave data.

In some embodiments, that system has an audio input device to receive audio signals corresponding to the music data.

In some embodiments, at least one computing device may be configured to generate a data structure with a tag on the music data, the tag defining an emotional state based on the EEG response.

In some embodiments, the EEG response defines a current physical state of the user and wherein the at least one computing device is configured to determine the recommendation based on a desired physical state relative to the current physical state.

In some embodiments, the system has an interface to a music platform for triggering download or purchase of the music data item of the recommendation.

In some embodiments, the system has an interface for displaying a current emotional state of the user based on the EEG response.

In another aspect, embodiments described herein may provide a system with a plurality of bio-signal sensors, each bio-signal sensor comprising at least one brainwave sensor; and at least one computing device in communication with the plurality of bio-signals sensor to continuously receive bio-signal data comprising brainwave data of a plurality of users. The at least one computing device may be configured to: detect an EEG response as a segment of the brainwave data at a time period; correlate the time period to music data to compute a segment of music data corresponding to the segment of the brainwave data of the EEG response; determine a collective emotional state of the plurality of users; and generate a music data item using the segment of music data and the collective emotional state.

In accordance with an aspect of embodiments described herein, the system of the present invention may find other users that have similar EEG responses to music as the user. For example, this can be added to web sites like Spotify and or dating web sites. For example, the system may only allow people into a private forum web site if they have had a strong enough emotional response to a song.

In accordance with an aspect of embodiments described herein, the system of the present invention may change mood through music, for example, for treating depression using music therapy.

In accordance with an aspect of embodiments described herein, the system of the present invention may use EEG for marketing or creation of music, by studying the EEG responses of people to new music to provide feedback to the creative process.

In accordance with an aspect of the embodiments described herein, there is provided a system with at least one computing device; at least one bio-signal sensor in communication with the at least one computing device; the at least one computing device configured to:

receive bio-signal data of the at least one user from the at least one bio-signal sensor, at least one of the at least one bio-signal sensor comprising a brainwave sensor, and the received bio-signal data comprising at least brainwave data of the at least one user; receive other information from or about the at least one user; and recommend at least one selection of music data to the at least one user based at least partly on the received bio-signal data and the other information.

In accordance with an aspect of embodiments described herein, there is provided the system of the present invention wherein the each of plurality of music data is associated with treatment for at least one mental state; the recommending comprising recommending at least one of the plurality of music data based at least partly on a determined correspondence between the respective associated mental state to be treated and the received bio-signal data.

In accordance with an aspect of embodiments described herein, there is provided a system comprising: at least one computing device; at least one bio-signal sensor in communication with the at least one computing device; the at least one computing device configured to: receive bio-signal data of the at least one user from the at least one bio-signal sensor, at least one of the at least one bio-signal sensor comprising a brainwave sensor, and the received bio-signal data comprising at least brainwave data of the at least one user; determine a correspondence between the received bio-signal data and bio-signal data available to the system associated with at least one second user; and trigger a user correspondence action based at least partly on the determined correspondence.

In accordance with an aspect of embodiments described herein, there is provided a system comprising: at least one computing device; at least one bio-signal sensor in communication with the at least one computing device; the at least one computing device configured to: present at least one digital content item to at least one user at the at least one computing device; receive bio-signal data of the at least one user from the at least one bio-signal sensor, at least one of the at least one bio-signal sensor comprising a brainwave sensor, and the received bio-signal data comprising at least brainwave data of the at least one user; determine at least one emotion exhibited by the received bio-signal data; and associate the at least one emotion with the presented at least one digital content item.

In accordance with an aspect of embodiments described herein, there is provided a method performed by at least one computing device, the method comprising the steps of the at least one computing device from the system of the present invention.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

Embodiments will now be described, by way of example only, with reference to the attached figures, wherein:

FIG. 3 shows an exemplary entry of brain state in a database in accordance with embodiments described herein;

FIG. 5 shows a table indicating user emotions before listening and after listening to a particular song;

Figure 1:
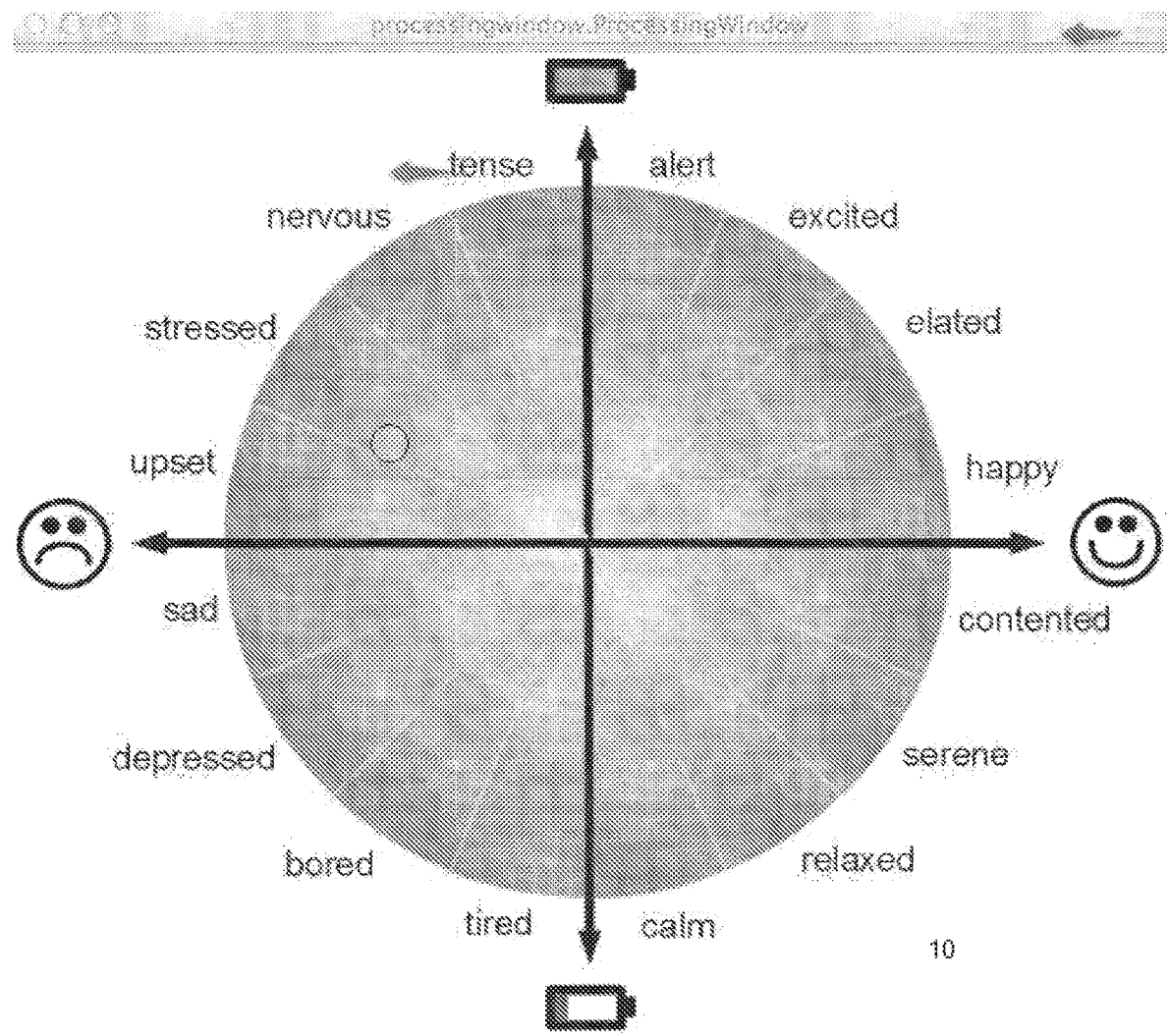
FIG. 1 illustrates a chart depicting valence-arousal dimensions for quantifying emotions.

In the drawings, embodiments are illustrated by way of example. It is to be expressly understood that the description and drawings are only for the purpose of illustration and as an aid to understanding, and are not intended as a definition of the limits of the invention.

DETAILED DESCRIPTION

A system and method is described associating bio-signal data (e.g. EEG brain scan data) from at least one user with at least one music data item (e.g. song, or piece of music). By associating bio-signal data, or emotions determined therefrom, with music, the system may establish a database of music associated with emotions. That database may then be leveraged upon determining that a user is feeling a particular emotion through an EEG scan. When a particular emotion is detected in EEG data of a user, the system may then respond based at least partly on the same or similar emotion being associated with one or more music data items in the system. For example, the system may recommend a particular song associated with the same emotion presently being experienced by the user. The system may then also begin playing that song. The database of music data and bio-signal or emotion data may be stored in a local computer or accessed on one or more servers, such as in the cloud. The music may be music that the user has access to or not. If the user does not have access to play the particular music data item recommended for playback, the system may also provide one or more options to the user for acquiring access to the recommended music data item (e.g. offer a choice to purchase the song or refer the user to a third-party service, retailer, or provider that may be able to provide access to the song to the user).

In accordance with aspects of the present invention, the computer system is provided that is implemented by one or more computing devices. The computing devices may include one or more client or server computers in communication with one another over a near-field, local, wireless, wired, or wide-area computer network, such as the Internet, and at least one of the computers is configured to receive signals from sensors worn by a user. In an implementation, the sensors include one more bio-signal sensors, such as electroencephalogram (EEG) sensors, galvanometer sensors, electrocardiograph sensors, heart rate sensors, eye-tracking sensors, blood pressure sensors, pedometers, gyroscopes, and any other type of sensor. The sensors may be connected to a wearable computing device, such as a wearable headset or headband computer worn by the user. The sensors may be connected to the headset by wires or wirelessly. The headset may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable computing device), external sensors (contained outside the wearable computing device), user effectors, and any servers may be encrypted. Collected and analyzed data may be used to build a user profile that is specific to a user. The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable computing device or other local computing device for providing feedback to the user, for example, to vibrate or provide some audio or visual indication to assist the user in achieving a particular mental state, such as a meditative state.

A cloud-based implementation for processing and analyzing the sensor data may provide one or more advantages including: openness, flexibility, and extendibility; manageable centrally; reliability; scalability; being optimized for computing resources; having an ability to aggregate information across a number of users; and ability to connect across a number of users and find matching sub-groups of interest. While embodiments and implementations of the present invention may be discussed in particular non-limiting examples with respect to use of the cloud to implement aspects of the system platform, a local server, a single remote server, a SAAS platform, or any other computing device may be used instead of the cloud.

In one implementation of the system of the present invention, a Multi-modal EEG Data-Collection and Adaptive Signal Processing System (MED-CASP System) for enabling single or multi-user mobile brainwave applications may be provided for enabling BCI applications. This system platform may be implemented as a hardware and software solution that is comprised of an EEG headset, a client side application and a cloud service component. The client side application may be operating on a mobile or desktop computing device. A particular system implementation may include a range of different features and functions, for example an EEG headset may be designed to target the meditation (such as health and wellness, or human-performance) market segment, and may be designed to be usable with other BCI applications. Non-limiting features of this headset may include: an unobtrusive soft-band headset that can be confidently worn in public; and use of 3, or 4, or more electrodes for measuring EEG data of the user. The system may provide for: estimation of hemispheric asymmetries and thus facilitate measurements of emotional valence (e.g. positive vs. negative emotions); and better signal-t-noise ratio (SNR) for global measurements and thus improved access to high-beta and gamma bands, which may be particularly important for analyzing cognitive tasks such as memory, learning, and perception. It has also been found that gamma bands are an important neural correlate of mediation expertise.

In the same or another non-limiting exemplary implementation, possible MED-CASP system features may include: uploading brainwaves and associated sensor and application state data to the cloud from mobile application; downloading brainwave & associated data from the cloud; real-time brain-state classification to enable BCI in games or other applications; transmitting real-time brain-state data to other users when playing a game to enable multi-user games; sharing brainwave data with other users to enable asynchronous comparisons of results; sharing brainwave data to other organizations or third party applications and systems; and support of cloud based user profiles for storing personal information, settings and pipeline parameters that have been tuned to optimize a specific user's experience. In this way, usage of the system platform can be device independent.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience). The core functionality of the MED-CASP system may be wrapped as an externally-usable library and API so that another developer may use the platform's features in the developer's application(s). The library may be a static library and API for Unity3D, iOS, Android, OSX, Windows, or any other operating system platform. The system platform may also be configured to use a pre-compiled algorithm supplied by a third party within the library, including the ability for a third party developer using the library, to use the developer's own algorithms with the library. The system platform may also support headsets from a variety of vendors; personal data security through encryption; and sharing of un-curated data (optionally using time-limited and fidelity limited access) though the sharing of encryption keys.

Optionally, the system of the present invention may be used to implement aspects of the systems and methods described in PCT Patent Application No. PCT/CA2013/000785, filed Sep. 16, 2013, the entirety of which is incorporated by reference herein. Accordingly, the system of the present invention may be or may be used with a computer network implemented system for improving the operation of one or more biofeedback computer systems. The system may include an intelligent bio-signal processing system that is operable to: capture bio-signal data and in addition optionally non-bio-signal data; and analyze the bio-signal data and non-bio-signal data, if any, so as to: extract one or more features related to at least one individual interacting with the biofeedback computer system; classify the individual based on the features by establishing one or more brain wave interaction profiles for the individual for improving the interaction of the individual with the one or more biofeedback computer systems, and initiate the storage of the brain waive interaction profiles to a database; and access one or more machine learning components or processes for further improving the interaction of the individual with the one or more biofeedback computer systems by updating automatically the brain wave interaction profiles based on detecting one or more defined interactions between the individual and the one or more of the biofeedback computer systems.

Optionally, the system of the present invention may be used to implement aspects of the systems and methods described in PCT Patent Application No. PCT/CA2013/001009, filed Dec. 4, 2013, the entirety of which is incorporated by reference herein. Accordingly, the system of the present invention may be or may be used with a computer system or method for modulating content based on a person's brainwave data, obtained by the sensors of the wearable apparatus of the present invention, including modifying presentation of digital content at at least one computing device. The content may also be modulated based on a set of rules maintained by or accessible to the computer system. The content may also be modulated based on user input, including through receipt of a presentation control command that may be processed by the computer system of the present invention to modify presentation of content. Content may also be shared with associated brain state information.

In accordance with an aspect of the present invention, there is provided a system comprising: at least one computing device; at least one bio-signal sensor in communication with the at least one computing device; the at least one computing device configured to: receive bio-signal data of the at least one user from the at least one bio-signal sensor, at least one of the at least one bio-signal sensor comprising a brainwave sensor, and the received bio-signal data comprising at least brainwave data of the at least one user; receive other information from or about the at least one user; and recommend at least one selection of music data to the at least one user based at least partly on the received bio-signal data and the other information.

In accordance with an aspect of the present invention, there is provided the system of the present invention wherein the each of plurality of music data is associated with treatment for at least one mental state; the recommending comprising recommending at least one of the plurality of music data based at least partly on a determined correspondence between the respective associated mental state to be treated and the received bio-signal data.

In accordance with an aspect of the present invention, there is provided a system comprising: at least one computing device; at least one bio-signal sensor in communication with the at least one computing device; the at least one computing device configured to: receive bio-signal data of the at least one user from the at least one bio-signal sensor, at least one of the at least one bio-signal sensor comprising a brainwave sensor, and the received bio-signal data comprising at least brainwave data of the at least one user; determine a correspondence between the received bio-signal data and bio-signal data available to the system associated with at least one second user; and trigger a user correspondence action based at least partly on the determined correspondence.

In accordance with an aspect of the present invention, there is provided a system comprising: at least one computing device; at least one bio-signal sensor in communication with the at least one computing device; the at least one computing device configured to: present at least one digital content item to at least one user at the at least one computing device; receive bio-signal data of the at least one user from the at least one bio-signal sensor, at least one of the at least one bio-signal sensor comprising a brainwave sensor, and the received bio-signal data comprising at least brainwave data of the at least one user; determine at least one emotion exhibited by the received bio-signal data; and associate the at least one emotion with the presented at least one digital content item.

In accordance with an aspect of the present invention, there is provided a method performed by at least one computing device, the method comprising the steps of the at least one computing device from the system of the present invention.

People listen to music in order to: (a) improve their performance on certain tasks (music helps us combat boredom and achieve our optimal levels of attention while driving, studying or working); (b) stimulate their intellectual curiosity (by concentrating and analysing the music we hear); and (c) manipulate or influence their own emotional states with the goal of achieving a desired mood state, e.g., happiness, excitement, and sadness. EEG can be analyzed to detect like and dislike. Some music databases may not use EEG or other bio-signal data but nevertheless have associated a mood or feeling with a particular music item, such as a song. For example, a user may be asked questions used to determine an emotional response to be associated with a piece of music. Questions may include: What was your song the last time you were really in love?; Think of a song that makes you feel sad?; Think of a song that makes you feel like dancing?; Think of a song that makes you feel inspired?; I am easy to difficult to get along with; When I feel sad: a) I listen to sad songs or b) listen to happy songs; I love karaoke or I hate karaoke; I like guitar bands or I am not a fan of guitar bands; I have a really few close friends or I have loads of friends; Body piercing can be attractive or body piercing can be a real turn-off; Life is basically simple or life is complicated; Music is all about memories for me OR I just like the music I like; My Favourite songs are sad songs OR My favourite songs are happy songs; Mess bother me OR Mess doesn't bother me; I work harder than most people I know OR I'm lazier than most people I know; I tend to worry about things OR I'm not a Worrier; I'm an Optimist OR I'm a pessimist; I hate fancy dress OR I love fancy dress; I don't get very emotional about things OR I'm a pretty emotional person; I feel uncomfortable dancing OR Love Dancing; I love meeting people and making friends OR I'm a bit shy around people I don't know; I hate it when the phone rings OR I love it when the phone rings. These questions may provide background profile of a person used to establish context for the types of songs a person likes to listen. The information can be thought of as training data that does not rely on EEG signals. The questions may determine a particular personality type of music enjoyment.

The present invention goes beyond merely asking questions, and associates bio-signal data (EEG brain scan data) from at least one user with one or more particular pieces of music or songs that the user is listening to. This invention also may add EEG data of the user as additional training data to songs that have been labelled by the user as evoking a particular emotion, through the user self-reporting the emotion either through the above questions, or by tagging a song manually.

Auditory Mirror Neurons and Entrainment

There is now evidence that humans have an auditory mirror neuron system that responds both when we perform actions and when we hear the sounds of those actions being performed, and that this system facilitates empathy. Audiovisual entrainment ("AVE") effects on the EEG are found primarily over the sensory-motor strip, frontally, and in the parietal lobe (somatosensory) regions and slightly less within the prefrontal cortex. It is within these areas where motor activation, attention, executive function, and somatosensory (body) awareness is primarily mediated. Auditory entrainment ("AE") is the same concept as visual entrainment, with the exception that auditory signals are passed from the cochlea of the ears into the thalamus via the medial geniculate nucleus, whereas visual entrainment passes from the retina into the thalamus via the lateral geniculate nucleus. Eyes-closed AVE at 18.5 Hz has been shown to increase EEG brainwave activity by 49% at the vertex. At the vertex (with the eyes closed) AE has been shown to increase EEG brainwave activity by 21%. Successful entrainment may lead to a meditative, peaceful kind of dissociation, where the individual experiences a loss of somatic and cognitive awareness. However, it is possible for visual entrainment to trigger seizures.

Other Physiological Markers of Emotion

A variety of physiological measurements are known to have been used to detect emotional states, such as galvanic skin response (GSRe), blood volume pressure (BVP), heart rate (HR), electromyogram (EMG), skin conductivity (SC), respiration amplitude and rate (RESP), electrocardiogram (ECG), the vertical component of the electrooculogram (EOG), the tonic and phasic element of the electrodermal activity (EDA), etc.

The anterior cingulate cortex (ACC) is responsible for emotion and it may be detected by EEG. The anterior cingulate cortex (ACC) may be divided anatomically based on cognitive (dorsal), and emotional (ventral) components. The dorsal part of the ACC is connected with the prefrontal cortex and parietal cortex as well as the motor system and the frontal eye fields making it a central station for processing top-down and bottom-up stimuli and assigning appropriate control to other areas in the brain. By contrast, the ventral part of the ACC is connected with amygdala, nucleus accumbens, hypothalamus, and anterior insula, and is involved in assessing the salience of emotion and motivational information. The ACC seems to be especially involved when effort is needed to carry out a task such as in early learning and problem-solving.

There is research focused on the relation between emotional processing and frontal alpha asymmetry leading to the development of the "hemispheric valence hypothesis". This hypothesis states that positive approach-related emotions are mainly processed in left frontal brain areas, whereas negative withdrawal-related emotions rather engage right frontal brain regions. In the EEG this is reflected by an asymmetric decrease of alpha power according to the perceived emotion, that is, a decrease of left frontal alpha power during positive emotions and a decrease of right frontal alpha power during negative emotions. There has been investigation of the trait-like frontal alpha asymmetry in the resting EEG of healthy subjects and different patient populations or the asymmetry of anterior cortical activity during stimulus induced emotional states.

Consonant and dissonant music generally may induce pleasant and unpleasant emotions in listeners, respectively. However, the impact of music on a listener is more complicated than determining dissonance and consonance. Emotionally intense music can stimulate the pleasure centres of people's brains even if the emotion is negative such as sadness or anger. Listening to emotionally intense music can relieve tension and be cathartic if a person cries for instance. Crying can relieve stress and elevate mood.

Emotionally intense music may cause dopamine to be released in the pleasure and reward centers of the brain, similar to the effects of food, sex and drugs. This makes us feel good and motivates us to repeat the behavior. The number of goose bumps observed correlated with the amount of dopamine released, even when the music was extremely sad. This suggests that the more emotions a song provokes—whether depressing or uplifting—the more we crave the song.

The choice of type of song depends on the current mood of the user. Also, when we are sad some of us prefer to hear sad songs and others prefer to hear happy songs when we are sad. The most important function of music is to influence our emotional state. By keeping track of current emotional state and state after listening to music, we can gauge the degree that the music has influenced emotional state—hopefully in a positive direction.

The present invention may determine the user's emotional response once, after a predetermined time has passed while playing a song, such as for example 5 seconds. Optionally, the present invention may take multiple samples of the user's emotional response throughout playback of the song, and time-stamp any determined emotional response to correspond to time codes of the playback position of the song. One or more of the detected emotional responses of the user may then be associated with the song. Other data may also be associated with the song or used to determine the user's emotional response, such as measure of engagement (e.g. focus and entrainment with music) and EEG valence. Other sensors or other context sensors may also be used to support the emotional response determination.

One or more determinations of error-related negativity ("ERN") may also be used to correct erroneous actions of the user.

Considerations when determining emotional response include: What is the moment to moment experience of people reaction to music?; Does person A react like person B does to the same piece on a moment by moment real time analysis?; What song do I listen to after this one?; Know—what songs do we listen to over and over. what do we skip? moment by moment allows more detailed analysis of music—vocals, bass rift, what point in the son gives us shivers; Spotify and track focus of people in music.

Issues with Categorizing Emotion

The full realm of emotion is difficult to quantify or measure in a scientifically-accurate, reproducible way. Even deciding on a language of emotion can prove difficult. This is why neuroscientists commonly use the Valence-Arousal dimensions (or VA dimensions) shown in processing window 10 of FIG. 1 to describe emotion. In these dimensions, Valence is one axis with "approach motivation" (feelings of positivity) on one end, and "avoidance motivation" (feelings of negativity) on the other. The other opposing axis is Arousal, with high intensity of feeling on one side and low intensity on the other. Commonly-felt emotions traditionally fall within the quadrants formed by that VA matrix.

Many people wonder where emotions actually come from. Scientists are now coming to the consensus opinion that the mind and the body are more closely linked than earlier Cartesian models of cognition might have indicated. For example, the muscles associated with performing an action have been determined to move approximately seven seconds before research subjects were consciously aware of having made the decision to perform the action. In other words, by the time you recognize you are thirsty and would like to take a drink, your hand is already reaching for a glass of water. This is just one example of the complex way in which the brain and the body are linked. Not all emotion lives in the brain, but not all action lives in the body.

With EEG, recognizing the total nuance of emotion can be difficult. But it's still possible. EEG is very good at noticing changes in the brain's state. EEG measures a series of responses to stimuli that occur in the brain. EEG can recognize responses associated with these feelings: recognition; error; novelty; sleepiness; focused attention; calm.

In accordance with an aspect of the present invention, these detectable emotions may provide a basis for various responses described herein, however the present invention is not intended to be limited to these. Further emotions may also be detectable, to varying degrees of accuracy and subtlety.

One way to improve emotion detection with EEG is to add more sensors to read more data not available from the brain, or to incorporate data from other sensors on other devices that a user is also wearing. Sensors in other wearable technology devices can read things like: temperature; galvanic skin response; motion; heart-rate and pulse; muscle tension through electromyography.

These types of data can indicated involuntary physical responses from which we can deduce emotion using filtering algorithms that strain out "noise" generated from extraneous stimuli. Additional data can help make a stronger case for one emotion or another. For example: an EEG might be able to sense a negative reaction to stimuli, but without contextual information from the user—either from the user's participation in an app environment, or from additional sensor data gleaned from other devices or other sensors of the system of the present invention—it might be difficult for the system to "learn" what precipitated that negative response. Perhaps the user heard a song she didn't like on the radio, or maybe she just saw a mouse run across her kitchen floor.

User Self-Report

The accuracy of recognizing emotion can be improved when a prediction is provided to the user based on the system's analysis of their EEG. The user can reject the system's prediction and correct it with their own experience. In this way, the accuracy of the models used to predict emotion can be improved through direct user manual override, using other measures of physiology related to emotion, context of the user (e.g. get information on the current activity from the user's calendar) and their behaviour (e.g. they skip over songs by artist X and they choose to listen to songs by artist Y.)

On Apps

Multiple user stories within this provisional patent refer to the use of apps by wearers of a wearable computing device of the present system. There is a specific user story related to app use below. However, it should be understood that other applications of the present invention are possible. All mention of "apps" may refer to applications included or provided by the system, or provided by a third-party to interface with the system.

These apps may be experienced, used, or interacted with in a variety of formats, including but not limited to: On the wearable computing device or devices; On a personal computer; On a personal mobile device, such as a phone or tablet or watch; On a website, in a browser-based application; In a vehicle equipped with the app in the dashboard or entertainment centre.

In accordance with an aspect of the present invention, an EEG controlled equalizer is provided that uses a control signal or test music to adjust the settings of an equalizer for a room based on the brain state of the user. The idea is to use Auditory Motor Neurons to: measure empathy in humans; use degree of empathy to drive neurofeedback among a group of humans who become empathetically synchronized to each other.

Definitions

Contextual Baseline Definition: The context of the user when using the system of the present invention. Context is defined by task or situation (e.g. at work or relaxing), weather, calendar appointment, time of day, location, goals of the user, who are the people with the user, external environment (e.g. room temperature, weather), and biological status of user (stressed, calm, emotional state etc.). The context is classified and the classification of the context can be used to select an algorithm pipeline to analyze and process the information received.

User Stories as Example System Architectures by Category

The following user stories may be intended to use system architecture that includes: cloud storage of user profiles; cloud data-mining to discover new algorithm pipelines and rules for processing the EEG; and manual override of prediction by the user to help improve prediction performance. The "user stories" described herein are intended to be exemplary implementations or embodiments of aspects of the present invention. The present invention is not intended to be limited to the precise steps or features described in the user stories. In fact, aspects of the present invention may be intended to be implemented in a more generalized manner than that described in the user stories. For example, any reference to a specific user is not intended to be limiting.

Example Application: Music Recommendation: Recommending Sounds Based on Emotional States An example application involves recommending sounds based on emotional states.

The following is an illustrative user story for this example application:
Jenny wears an EEG-reading device and an audio analyzer that contains a microphone
As Jenny goes about her daily tasks, the microphone continually listens to the ambient sounds around her. (INPUT)
As the microphone listens to the ambient sounds, the EEG scanner is logging Jennys emotional state (INPUT)
Jenny's emotional state is then logged along with the ambient sounds into a database, either stored locally on her device or on a remote server via the Internet on in the cloud (INPUT)
As Jenny listens to more and more music and visits more and more places, an algorithm on her mobile device or on a remote server (in the cloud or accessed via the Internet) pairs her emotional states with the ambient sounds that are collected in her daily travels (PROCESS)
Over time, a profile is built that correlates her emotional states with the ambient sounds that accompany them (PROCESS)
When the profile reaches maturity a program on Jenny's mobile device (or running on a remote server, accessed over the Internet or in the cloud) informs her which kinds of ambient sounds are related to which emotions (PROCESS, OUTPUT)
i.e. a car horn makes her anxious; a purring cat makes her relaxed; waves crashing on the beach make her happy
When Jenny wants to achieve a certain emotional state, she queries either her device or a remote server (via the Internet or in the cloud) and the device or server will play back a sound that's associated with her desired emotional state (happy, calm, etc) (PROCESS, OUTPUT)
Jenny becomes more aware of which kinds of sounds produce which kinds of emotional states
The value proposition for this user story may include:
There is a large market for behaviour modification tools because people want to be able to induce different types of emotional states (calm when anxious, etc). This process could be used in conjunction with a meditation program or similar. Sounds are very intimately tied to emotional states Sensors used in this user story may include:
EEG, heart rate (stress), galvanic (stress)

Example Application: Music Recommendation: Tagging Music to Emotional States

An example application involves tagging music to emotional states.

The following is an illustrative user story for this example application:
Brutus is shopping in a store and hears a song playing over the PA system—Dingbat Love—while he is wearing an EEG-sensing device and a microphone attached to his mobile device
While Brutus listens to Dingbat Love while shopping, his EEG device recognizes that he likes the song very much (INPUT)
The microphone Brutus is wearing is continually sampling the audio environment around him (INPUT). This audio data is either stored locally on Brutus' device or it is stored on a remote server via the Internet or in the cloud
When the EEG device detects that Brutus likes a song, this preference is either recorded on his mobile device or on a remote server (INPUT). Thus, a trace of Brutus' song preference is now recorded
Over time, a profile of Brutus' preferred songs is built and stored on either his mobile device or on a remote server, accessed via the Internet or the cloud
When the EEG system detects that Brutus likes a song, a music-recognition app (like Shazam) is automatically launched (PROCESS, OUTPUT)
The recognition app recognizes Dingbat Love (PROCESS, OUTPUT)
Brutus buys the song when prompted to do so (PROCESS, OUTPUT)
The system suggests songs and artists similar to Dingbat Love so Brutus can purchase additional music (PROCESS, OUTPUT)
The value proposition for this user story may include:
With the use of an EEG scanner and a microphone, music marketing can be tailored to individual tastes (narrowcasting) rather than to large groups (broadcasting), adding increased value
The sensors used may include: EEG, microphone.

Example Application: Music Recommendation: Tagging Sounds to a Specific Location An example application involves tagging sounds to a specific location.

The following is an illustrative user story for this example application:
Jaleel wears an EEG-sensing device and a microphone-enabled listening device when he's out and about during the day
Jaleel listens to music while he performs his tasks
The microphone constantly listens to the ambient sounds of his environment and records those sounds, either locally on his device or on a remote server accessed via the Internet or in the cloud (INPUT)
Either Jaleel's portable device or a remote server detects when Jaleel is happy (PROCESS).
The device correlates the happy emotion with the sounds from his external environment (PROCESS)
Jaleel's GPS sensor records the location where this correlation takes place (INPUT)
Either Jaleel's portable device, or a remote server accessed via the Internet or in the cloud, builds a profile of locations where Jaleel hears "happy sounds" (PROCESS)
In a separate process, Jaleel has tagged songs on his mobile device that he likes to listen to
When Jaleel reaches the GPS co-ordinates that correspond to his "happy places", his mobile device automatically plays the songs he likes to hear (PROCESS, OUTPUT)
The value proposition for this user story may include:
Both listening to music and seeing specific geographical locations (where a person had their first kiss, etc) are highly evocative stimuli. This methodology combines those factors and adds music to the experience, which is also highly evocative
Sensors used may include: EEG, microphone.

A map of public places that people have associated feelings about may be called Emomapping (an emotional map of a city based on sound). Customer satisfaction of sound or music: theatre manager—knowing how people feel about the quality of sound in a place. Map quietest, bird songs locations, loudest, scientists ask birders which birds they see and hear. First Kiss places share magical places in the city. Big feed of how sounds characterize a city.

Sounds are disappearing nostalgia capturing memory of sound—sounds are disappearing like rotary dial phone, leaded gas engine, old songs, old arcade games, old video game sounds. Sounds of cars like diesel—going away. Bird song. Sounds of language in a neighbourhood as demographics shift hear different languages on the sidewalk. Lose sound of bells of churches if they move. Emotional resonance to different sounds. Apply to schools, museums, think about how house sounds during different times, monitor sounds of breathing like baby monitor—apply to sound of home. The data on how people feel about sounds is the value. Value prop is we are going to make the ultimate baby monitor.

Figure 2:
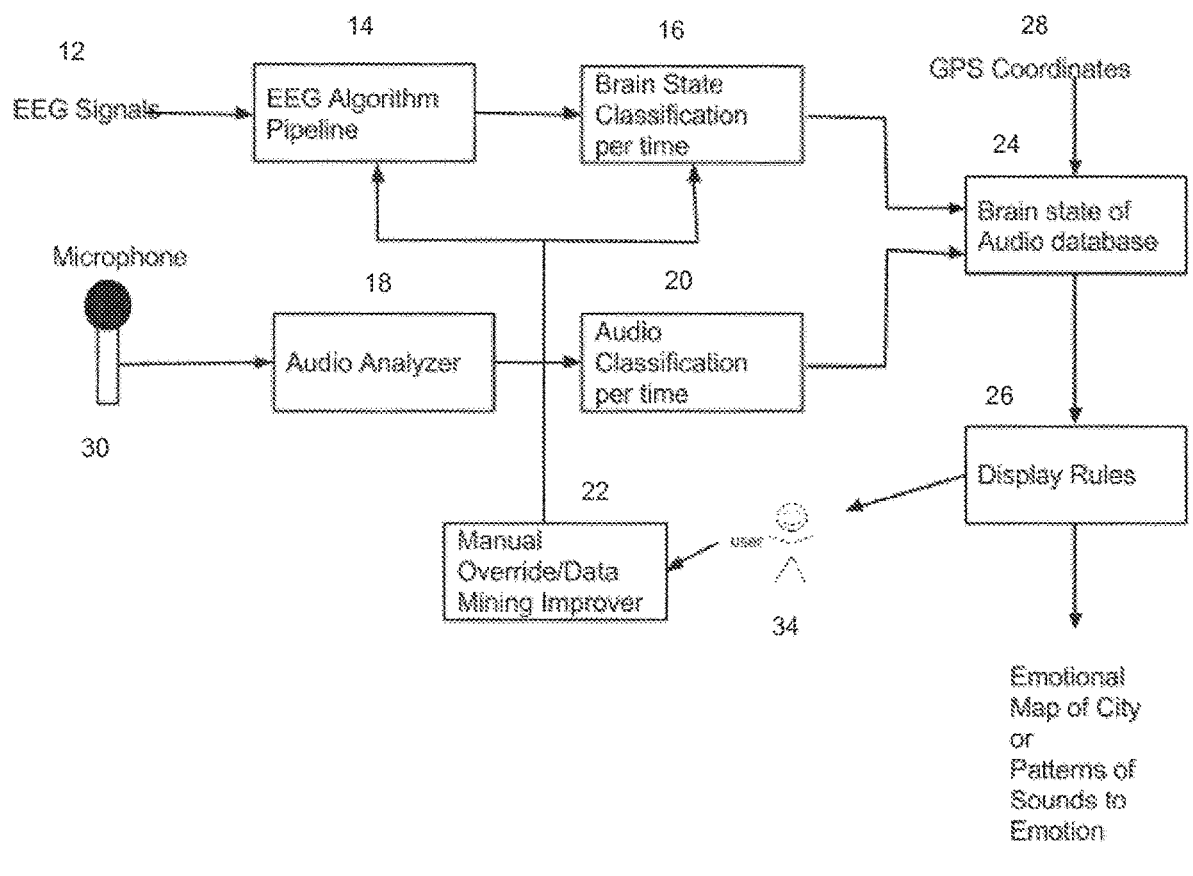
FIG. 2 shows an exemplary system view for the system in accordance with embodiments described herein.

FIG. 2 shows an exemplary system view for the system of the present invention as optionally implemented user stories recommending music based on emotional states.

An algorithm pipeline 14 is chosen based on the context. In this case the context is creating a database of classified sound and its associated brain state. An algorithm pipeline ID is chosen to pre-process the EEG 12, extract features. The features are sent to a Brain State Classification model that outputs a brain state classification 16 for a brief interval of time—example 1 second. The classification model could be based on prior samples of EEG generated by the user when listening to a sound. At the same time and using the same timestamps to label the EEG data 12, incoming audio via microphone 30 that the user hears is classified per unit time as well using an audio analyzer 18 that extracts features of the sound. The audio features 20 are classified per the same unit time as the EEG brain states. These audio classifications 20 are combined into the Brain state of Audio database 24. Examples of entries of the database are shown below. The database could be datamined for statistics or patterns. In addition, location information (e.g. GPS coordinates 28) can be associated with the same time interval as the audio information. The Display Rules 26 could build output 32 as a colour coded map of a city or area of brain state with audio category. The Display Rules 26 may also concatenate together shorter segments of time into an average brain state over a longer time interval. In addition, the user 34 can do a manual override 22 of the classification as shown by the Display Rules 26. The user can revise the estimate of the classification of Brain State Classification 16 (and Audio Classification 20). Based on the revised input provided the user, A Data Mining Improver 22 (shown in combination with manual override 22) can alter the methods for features extraction and the model of the Classifier. The user's input could have higher weighting when building a new model for classification.

FIG. 3 shows an exemplary entry 40 of brain state in a database in accordance with aspects of the present invention.

Example Application: Music Recommendation: User Override of Music Recommendation This example involves providing a "life soundtrack".
The following is an illustrative user story for this example application:
- Anton frequently participates in a variety of activities that include listening to music, like riding his bike or riding around the city on his skateboard. He listens to music on his mobile device. Tracks are either stored locally, on a remote server accessed via the internet, or in the cloud
- Anton wears an EEG-reading device while he performs these activities and while he listens to music
- As Anton performs his favourite activities, the EEG scanner is constantly observing his brain states and recording the activity, either locally on his mobile device; or in the cloud; or on a remote server accessed via the Internet (INPUT)
- An algorithm running on either the mobile device or on the remote server is constantly monitoring Anton's brain state, looking to see if he is happy or sad (PROCESS)
- The algorithm detects that Anton is in a "happy" emotional state while he is riding his bike (INPUT, PROCESS)
- The algorithm then suggests a song to listen to that Anton has previously tagged as "exciting" or "happy" (PROCESS, OUTPUT)
- As Anton listens to music on his mobile device, he's invited to "tag" songs with emotional states
- This tagging can either be done manually, or automatically based on EEG brain state data (INPUT). User can provide manual override of the musical recommendation. This can help improve the classification of the system and improve the accuracy of the music recommendation engine customized to this user. This is done through the Data Mining Improver.
- A profile of songs correlating to emotional states will be built up over time. This is stored in the User's Profile.
- Based on Anton's tags, the algorithm can suggest songs to play that correlate with other emotional states (sad, curious, etc) (PROCESS, OUTPUT)
- When Anton listens to music that correlates to his emotional state, the algorithm can also suggest similar songs for purchase The value proposition for this user story may include:
- Music is very highly associated with particular emotional states. This powerful emotional connection can be leveraged to provide sales opportunities for new music purchases.

Sensors used may include: EEG, heart rate (stress), galvanic (stress)

Figure 4:
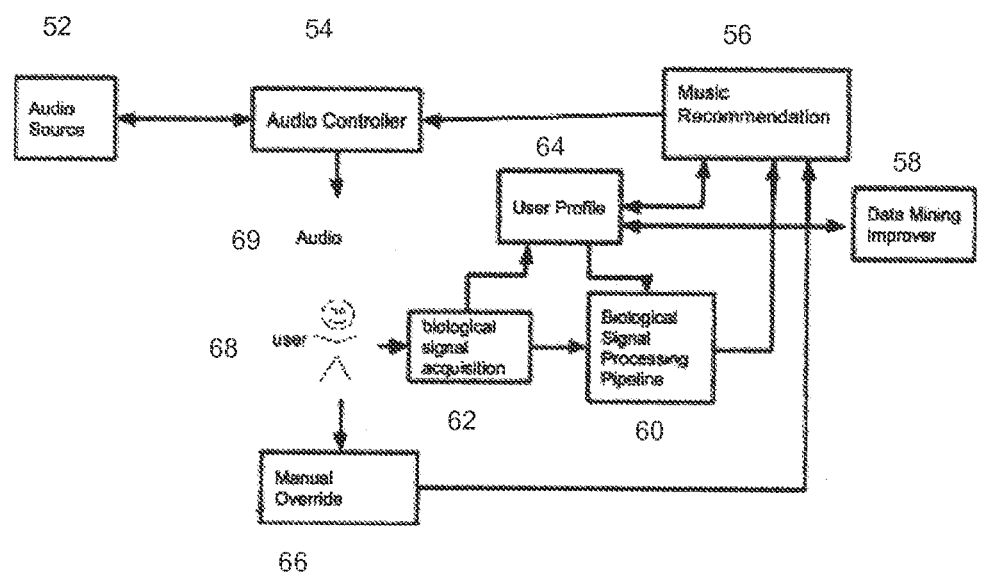
FIG. 4 shows a system view of user override of music recommendation in accordance with embodiments described herein.

FIG. 4 shows a system view of user override of music recommendation in accordance with an aspect of the present invention.

The Biological Signal Processing Pipeline 60 outputs a brain state to the Music Recommendation engine 56 of the initial brain state of the user before any audio plays. The Music Recommendation engine 56 selects an audio track 69 from an audio source 52 through the audio controller 54. This audio track 69 is played to the user 68. The user's 68 brainwaves are continuously analysed (via e.g. biological signal acquisition 62) while the audio track 69 plays. At any point the user may decide to input a Manual Override 66 to the system and say that this piece of music does not match my current mood which the user can input to the system. The Data Mining Improver 58 can update the Music Recommendation rules and feature extraction and EEG classification through the User's Profile 64.

Manual override is an optional feature of the present invention.

FIG. 5 shows a table 70 indicating user emotions before listening and after listening to a particular song.

Recommending Sound Based on User's Brain Response to Music

Johnny listens to music while wearing an EEG intelligent music system. The EEG could be embedded in the headphones, with sensors for example on the band at c3 and c4 and on the ears.

The EEG connects to a processing platform (e.g. smartphone, music player). The Processing Platform can also connect with the cloud.

Johnny's EEG and characteristics of the music are stored and analysed in the cloud.

When Johnny's brain state suggests liking of the music, for example and increase in left front activity, or an ERP, those aspects of the music can then be logged.

Those like characteristics are then compared to other music to choose music with similar characteristics which Johnny may also like, and that music is recommended to Johnny. This can also be used to compare how Johnny's brain responds to music with how other users brains respond to music, and similar reactions can trigger similar recommendations. For example "people who exhibited EEG patterns like yours while listening to X piece of music, also like Y piece of music".

Example Application: Music Recommendation: Matching Music to Physical States

This example application involves matching music to physical states.

The following is an illustrative user story for this example application:
- Jesse listens to music extensively while performing physical activities, like running or bike riding
- She performs these activities while wearing an EEG-sensing and a heart-rate-sensing device
- A series of songs are stored on either her mobile device or on a server accessed via the Internet, or in the cloud
- Over time, as Jesse listens to songs on her mobile device, she either manually tags them as something she likes to listen to while she does exercise, or an algorithm that listens to her EEG signal does so by correlating an EEG state corresponding to increased physical activity to the song that she's listening to (PROCESS, INPUT)
- When Jesse begins to perform physical activity, this is detected by sensors (EEG, heart rate) (INPUT, PROCESS)

An algorithm either stored locally on her mobile device, or accessed via the cloud, begins playing music (PROCESS)

Metadata about the songs on Jesse's device contains information about the format of the music, such as beats per minute (bpm)

An algorithm on Jesse's device (or accessed via the cloud) matches the selection of music based on beats per minute to the rate of her physical activity (as detected by heart rate sensors, etc) (PROCESS, OUTPUT)

The value proposition for this user story may include:

Music and fitness go hand-in-glove; there are many apps that currently exist that provide an exercise plan and allow music to be played simultaneously. This application will allow music to be intimately connected with the user's emotional state Sensors used may include: EEG, heart rate.

Example Application: Music Recommendation:
Detection of Songs Users Like

This example involves detection of songs users like.
The following is an illustrative user story for this example application:

Phil is listening to a selection of new music on his mobile device. The tracks are stored either locally on his device, on a server accessed via the Internet, or in the cloud Phil listens to his music while wearing an EEG-tracking device which actively scans his brainwave patterns while he listens. (INPUT)

As the tracks play, Phil's brainwave scanner detects his emotional states for each song (INPUT)

An algorithm residing either in Phil's mobile device or located in the cloud detects when Phil has a positive emotional response to a song (INPUT, PROCESS)

The song is automatically tagged as one of Phil's favourites (PROCESS)

After the song is tagged, the algorithm searches for similar songs based on online metadata (PROCESS)

The algorithm suggests additional songs that Phil can purchase based on his positive mental states The value proposition for this user story may include:

Data about users' positive emotional states can be sent to music producers and retailers. They can base marketing strategies directly on listener's emotional reactions to similar music, offering an unprecedented level of accuracy Sensors used may include: EEG.

Figure 6:
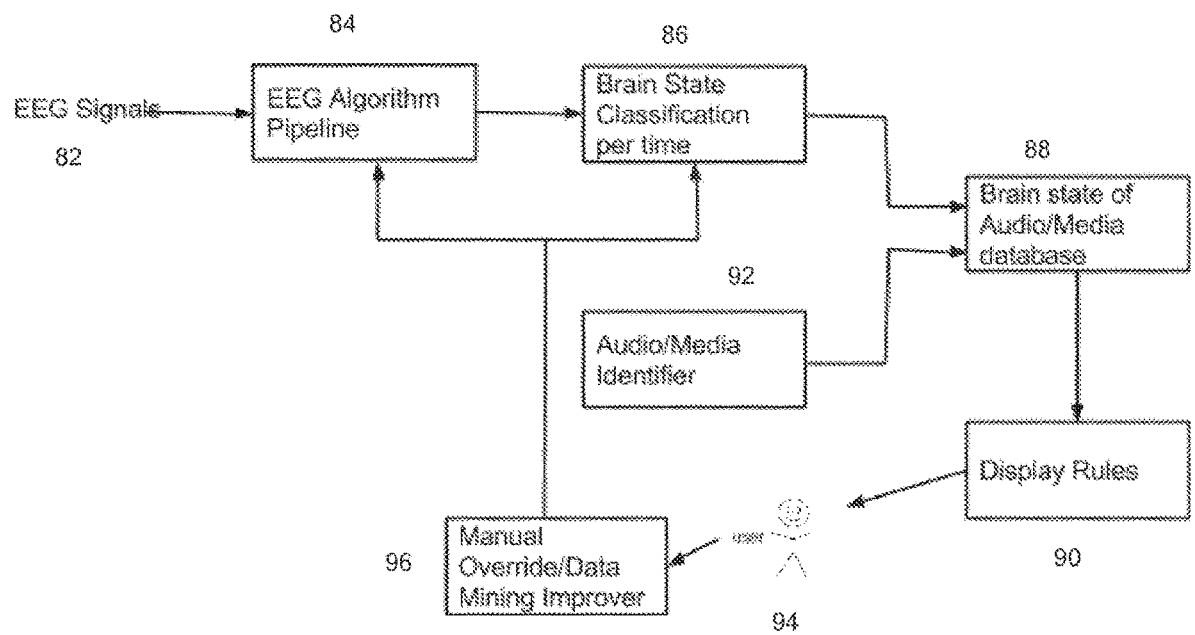
FIG. 6 illustrates an exemplary architecture in accordance with embodiments described herein.

FIG. 6 illustrates an exemplary architecture of the present invention, in particular for implementing this user story. FIG. 6 shows EEG signals 82 analyzed by the EEG Algorithm Pipeline 84. The pipeline 84 extracts features from the signal 82. These features are used by the Brain State Classifier 86 to output a prediction of user's brain state on a per time segment basis. An audio and or media identifier 92 is output from for instance an digital audio player that identifies the artist and piece of music (or other media such as television show or YouTube video etc.). The pieces of media are labelled on a per time segment basis with the predicted Brain State and are stored in the Brain State Audio/Media database 88. Display Rules 90 can display to the user 94 on a per time segment basis the predicted brain states of the user to the audio or media. In addition, Display rules 90 can process the predicted Brain States into for instance an average or a total percentage of a brain state across the entire media piece. Other Display Rules 90 are possible. The user 94 has the ability to manually over-ride the prediction provided through the Display Rules. This manual over-ride 96 can be used to improve the accuracy of the Brain State classifier 86 and or the EEG algorithm pipeline 84.

Example Application: Music Recommendation:
Using EEG Data to Track Media Preferences This example application involves using EEG data to track media preferences.
The following is an illustrative user story for this example application:

Gil is an avid consumer of television programming, He wears an EEG-reading device while he watches TV As Gil watches a series of programs, his EEG monitor is constantly monitoring his brainwave state. This information is continually processed by either a locally-based computer or is sent to a remote server via the internet or is sent for storage in the cloud for later processing (INPUT, PROCESS)

When Gil's EEG device recognizes that he's enjoying a program, a record of what he's watching is recorded either locally, on a remote server, or is stored in the cloud for later retrieval (INPUT, PROCESS)

The recording of the show Gil is watching can take 2 forms:

The system can store audio patterns from the program, which can be stored on a local computer or on a remote server over the Internet or stored in the cloud for later access. These audio patterns can then be analyzed for program content manually or algorithmically by a computer Many audience-participation measurement systems rely on a special audio frequency which encodes metadata about the program being watched. Gil's microphone can pick up these audio frequencies and thus immediately transmit information about which program he's watching when his EEG scanner determines he's enjoying the program Analytics about which programs Gil enjoys watching can automatically be sent to ratings agencies, etc Analytics about which programs Gil enjoys can lead to recommendations of new content for Gil.

The technology described above could also be deployed to determine the popularity of other media, like radio and recorded music The value proposition for this user story may include:

Trying to determine which television and radio segments are popular is a huge industry which consumes a lot of resources. Plus, traditional ratings systems only measure media that people are watching—there is currently no methodology for determining if viewers are actually enjoying the show or if they would enjoy similar programming. This methodology would allow for programmers to tailor their materials specifically to what the audience enjoys, and tailor recommendations to user's preferences.

Sensors used may include: EEG, microphone.

Example Application: Music Recommendation:
Sound Selection

This example application involves sound selection.
The following is an illustrative user story for this example application:

Bill is listening to a selection of his music on a portable device. The tracks are either stored locally on the device; in the cloud; or are accessed from a remote server over the internet. Bill is wearing an EEG-detection device while he listens to the music The system includes a pre-programmed sonic probe that is triggered by an algorithm to be played at the conclusion of each track The "probe" consists of an odd or unusual sound (OUTPUT).

Bill listens as the "probe sound" plays (PROCESS, OUTPUT)

The EEG device records Bill's reactions as he listens to the probe sound (INPUT, PROCESS)

The EEG device references Bill's brain state to determine his reaction to the probe sound If Bill records a positive response to the probe, that reaction indicates what kind of music is going to play next (PROCESS)

For example, if the EEG recording detects that Bill has a positive response to a "harsh" probe sound, then an algorithm, either running on Bill's mobile device, or on a remote server accessed via the internet, will instruct Bill's mobile device to play a "harsh" piece of music next, like heavy metal or industrial music (PROCESS, OUTPUT)

Similarly, if Bill's EEG detects a positive response to a "soothing" probe sound, the algorithm will instruct Bill's device to play a "soothing" piece of music next, like light jazz or classical music

OR

Instead of a "probe sound", the system instead plays a "musical blitzkrieg"—a sequence of very short musical clips As Bill is listening to the "blitzkrieg", his EEG detector is monitoring his brain state When a positive emotional response is detected, a log is made of which song achieves this result A similar log is created when the user registers a negative emotional response In this way a profile is created indicating what type of music creates a certain emotional response. Bill can then pick what songs he wants to listen to based on what emotional response he wishes to experience The value proposition for this user story may include:

Music is very closely tied to emotional states. This algorithm allows the user's emotional state to "pick" the next song they're going to listen to. The system can also suggest new songs for purchase based on the type of music the user is enjoying, as determined by EEG measurements. Possible marketing opportunity Sensors used may include: EEG.

Example Application: Music Recommendation: Music Selection Appropriate to Reading This example involves music selection appropriate to reading.

The following is an illustrative user story for this example application:

Nancy likes to read books, magazines and other periodicals while she listens to music Nancy finds her selection of music does not always appropriately match the "tone" of the reading material she has selected Nancy now reads while listening to music whilst wearing an EEG-detecting device As she reads, her mobile device plays out a playlist of music, which is initially random (PROCESS, OUTPUT)

As Nancy listens, her EEG device records her emotional response to the song that she's currently listening to. The algorithm that drives this process resides either locally on her mobile device or is accessed on a remote server via the internet. Alternatively, the brain state data is stored in the cloud for later retrieval (INPUT)

If Nancy's EEG reader detects a positive emotional response to the music she's listening to, this track is tagged in a playlist as being suitable for reading (INPUT, PROCESS)

Similarly, if Nancy elicits a negative emotional response to a particular track, the track is tagged as being unsuitable for listening to while reading (INPUT, PROCESS)

As Nancy continues to read and continues to listen to music, a playlist based on her preferences will gradually emerge. The more she listens while reading, the more accurate the playlist will become. (PROCESS)

An algorithm on Nancy's mobile device (or on a remote server) will thus be able to predict which songs match her preference for reading and will play those songs when she reads (PROCESS, OUTPUT)

The value proposition for this user story may include:

Many people read while listening to music. This process makes the two activities more compatible. There is also a marketing opportunity to suggest purchasing new songs for reading based on an individual's "reading profile"

Sensors used may include: EEG.

Example Application: Music Recommendation: Decreasing Stress while Driving

This example application involves decreasing stress while driving.

The following is an illustrative user story for this example application:

Nancy likes to listen to the radio while she drives. She wears an EEG-sending device while she drives Additional sensors might include heart rate to measure stress and galvanic skin response, also to measure stress Nancy often finds music and/or talk on the radio distracts her and makes her angry, impairing her performance behind the wheel As she drives, the EEG device measures Nancy's responses to the music she's listening to (INPUT)

An algorithm, running either on a local computer in Nancy's car, or on a server which is accessed via the internet, monitors Nancy's brain state.

When a negative mood is detected (INPUT) the algorithm immediately changes the radio station or the music selection that Nancy is listening to (PROCESS, OUTPUT)

Nancy's EEG monitors continually scan her brain state while she listens to her new musical/radio selection. If a negative emotional response is detected, the algorithm immediately switches the selection again until a positive mental state is achieved. (PROCESS, OUTPUT)

The value proposition for this user story may include:

The emotional state of drivers is intimately connected with their performance behind the wheel. The Ontario Driver's Handbook states a driver should not attempt to operate a motor vehicle if they are in a compromised emotional position. This tool could help drivers stay safe by ensuring the auditory stimulation they receive is positive in nature Sensors used may include: EEG; heart rate (stress); galvanic (stress).

Example Application: Music Recommendation: Enhanced Audio Content for Museums and Galleries This example application involves enhanced audio content for museums and galleries.

The following is an illustrative user story for this example application:
Martin enjoys visiting galleries and museums
When he visits a particular gallery, he is given an audio headset tour guide that incorporates an EEG sensor
As Martin tours the museum, the audio headset tour device plays musical selections when he stops in front of each work of art (OUTPUT)
As Martin views the art, an algorithm residing either locally in the tour device, or accessed via a remote server via the Internet, is reading his brain state (INPUT)
If the algorithm detects a negative response from Martin's brain state, the music is changed (by gently crossfading) (PROCESS, OUTPUT)
This process continues until Martin's brain state gives a positive reading (PROCESS, OUTPUT)
The value proposition for this user story may include:
Nearly every major gallery or museum around the world uses audio tour guide devices. Adding brain state detectors would add value and allow the museum or gallery to stand out amongst its competitors
Sensors used may include: EEG.

Example Application: Music Recommendation: Music & Focus (L1 MR)

User stories included: 1.13.
The following is an illustrative user story for this example application:
Morwenna wants to listen to music to help her focus on a task. Luckily, the system of the present invention may help her do this.
First, the system has to learn her preferences. She puts on the devices before sitting down to work.
Through headphones of the system, the device plays a selection of music while the brainwave scanner performs a scan using bone conduction, heart-rate detection, and galvanic skin response.
From these sensor Outputs, the system puts together a contextual baseline Brain State for Morwenna.
With the baseline in place, the system can establish differences between Morwenna's Brain States depending on stimuli or activity.
The system uses the sensors to "listen" to find which music puts her in a relaxed Brain State.
Over time, the system app builds a playlist for Morwenna called "Focus." This is all the music that has helped Morwenna to relax in the past.
Now every time she needs to focus, Morwenna can play her "Focus" playlist.
Over time, Morwenna can use the system to build other playlists bases on her emotional needs.

The value proposition for this user story may include:
This functionality allows listeners using the system device to correlate specific music with specific emotional states.
Sensors used may include: Brainwave (bone conduction), heart-rate, galvanic skin response (stress).
Applications may include: Listening to music privately; sharing music over social networks; improving productivity.

Example Application: Music Recommendation: Matching Music to Physical States (L1-MR)

User stories included: 1.11.
The following is an illustrative user story for this example application:
Snoop wants to go for a run—he informs his mobile device, which is connected to the wearable computing device of the system of the present invention, the wearable computing device incorporating or connected to one or more sensors, optionally attached to a headband, and headphones worn by Snoop.
Snoop activates a music-based fitness app that lives in his wearable computing device. The app connects Snoop's music library (either in the cloud or stored locally on his phone or other mobile device) to his wearable computing device headband and headphones.
As Snoop starts to run, his heart-rate rises.
An algorithm matches the beats per minute (BPM) of song to the BPM of Snoop's heart.
This provides Snoop with a sense of when he is slowing down that goes beyond the purely physical or internal. He can literally "hear" when he slows down, like a clock that needs to be wound. This is an easier Output for him to understand than looking down at a heart-rate monitor, or alternative device with less legible outputs and interfaces.
This more naturalistic interface allows Snoop to gain more pleasure from running, which encourages him to run more. Now that he runs more, he's improving his cardiovascular health.
The value proposition for this user story may include:
This functionality of the system of the present invention allows the user to gain a more naturalistic understanding of when they are slowing down during a physical activity, and provides a more enjoyable prompt to help them speed up during exercise. Also, it adds value to mobile music and fitness apps.
Sensors used may include: Heart-rate monitor (skin), bone conduction, temperature.
Applications may include: Physical fitness, personal training, music developers, physical therapists.

Example Application: Music Creation: Augmenting the Creation of or Listening to Music Using Brainwave Activity This example application involves augmenting the creation of or listening to music using brainwave activity.
The following is an illustrative user story for this example application:
John is a classical music composer working on a new symphony
While he is working on his symphony he has an audience of several people over to his studio to listen to his creation. They are all wearing brainwave sensing technology John plays several variations on a theme to his audience. He wants to pick the variation that produces the most significant emotional response.

John plays each variation. As the audience listens the response from their brainwave sensing devices is recorded, aggregated and analyzed on a server (INPUT, PROCESS). The server can either be based locally in John's studio on in the cloud The server looks for indications that the music is pleasurable to the listeners (i.e. searches for p300) (PROCESS)

Alternatively, John can program the server to look for whichever emotional response he desires (INPUT, PROCESS)

Alternatively John can aggregate data from other sensors (i.e. gyroscope) to detect other physical phenomena that he wants to elicit from the audience (like swaying to the beat or dancing in a chair) (INPUT, PROCESS)

The number of desired events elicited amongst the audience is recorded (INPUT, PROCESS)

John chooses the variation that elicits the greatest number of brainwave events that he desires The value proposition for this user story may include:

This technology allows the user to create a piece of music that elicits particular emotional reactions Sensors used may include: Brainwave, temperature, motion Example Application: Music Creation: Creating a Personal Sonic "Signature" for an Individual Based on their Music Preferences This example application involves creating a personal sonic "signature" for an individual based on their musical preferences.

The following is an illustrative user story for this example application:

Chad listens to a selection of music on his mobile device

As he listens, his mobile device gathers information about which tracks are his favourites, based on playlist frequency, etc (INPUT)

Over time, the device recognizes and collates Chad's favourite tunes (PROCESS). The tracks can either be stored locally on his device or they can be streamed from the cloud via a service like Radio Alternatively, a visitor to an art gallery or party can create a sonic signature on demand Jack is asked by the computer running the installation to input 3 of his favourite songs (INPUT)

The songs are retrieved either from a local server or via the cloud

The computer/server creates a synthesis of these songs to produce a "sonic signature" (PROCESS, OUTPUT)

When the algorithm has had sufficient exposure to Chad's music to perform an in-depth analysis, the algorithm—extracts a sonic "signature" (similar to Shazam) from each tune and then blends them together (PROCESS)

This "melded" soundscape becomes Chad's personal "sonic signature"—belonging to him and him alone (OUTPUT)

This "sonic signature" can be played as a ringtone or similar (like as a chime when exchanging data with another user). The "signature" is stored locally on Chad's device If Chad is wearing Google Glass, the "signature" can be played out as a warning tone if the AR device detects danger (i.e. while driving, biking, etc)

As Chad listens to his music, a high-resolution "data map" of his EEG responses to the track being played are recorded The recording can capture other physiological states, such as heart rate, galvanic skin response and eye tracking (INPUT)

This physiological information is tracked to the music on a second-by-second basis (INPUT)

As the music plays, a "physiological record" of how the music is affecting Chad can be generated (PROCESS)

This "data map" can be compared from person to person to see if two people have compatible musical tastes, etc (OUTPUT)

The value proposition for this user story may include:

In a world where mobile devices and data are proliferating, people can feel anonymous. This "sonic signature" can give a measure of personality to the device(s) owned by the user Sensors used may include: EEG, accelerometer (for danger sensing).

Example Application: Music Creation:
Focus-Driven Musical Selection

This example application involves focus-driven musical selection.

The following is an illustrative user story for this example application:

Linda is bored listening to her familiar mix of music on her mobile device

She logs onto an internet site whilst wearing an EEG-reading apparatus

She downloads a track that's been created by an artist over the cloud. The track is either streamed from the cloud or is stored locally on the device (INPUT)

As she listens to the new track, the EEG device monitors her brainwave state (PROCESS)

The EEG device detects which part of the music she's paying attention to (e.g. vocals or a specific instrument) (PROCESS)

An algorithm increases the "presence" of that element of the music while "toning down" the other elements of the song (PROCESS, OUTPUT)

As Linda continues to listen to the piece her focus will shift to other components of the track. The algorithm performs the same function again, bringing the new element of the song into "focus" while reducing the other elements (PROCESS, OUTPUT)

The value proposition for this user story may include:

This process helps to personalize a user's listening experience so they focus on the elements of a song they find the most pleasurable/useful Sensors used may include: EEG.

Example Application: Music Creation: Using Music to Make a Group of People Aware of the Collective Emotional State of the Group This example application involves using music to make a group of people aware of the collective emotional state of the group.

The following is an illustrative user story for this example application:

At a restaurant, each booth is equipped with a speaker which is linked to a centralized database containing music. Alternatively, the music is streamed from the cloud Each diner wears an EEG-sensing headband that is in communication with the computer/server/cloud that plays out the music As the diners eat, the EEG headband monitors their moods (INPUT, PROCESS)

The moods of the diners are correlated to the type of music that plays.

When the moods are pleasant, music that is harmonious and synchronized is played (PROCESS, OUTPUT)

When the EEG sensor detects a foul mood, discordant music begins to play (PROCESS, OUTPUT)

When the waiter/waitress passes by a particular booth, they can immediately intuit whether the diners are happy or not.

If the diners are not happy, the waiter/waitress can do something to try to rectify the situation The value proposition for this user story may include:

Many people are too shy to say out loud if they are unhappy with customer service. They voice their displeasure by not attending the business again or, even worse, by recommending by word of mouth that people they know should not attend. Using this technology a business can nip negative attitudes in the bud as they occur in realtime to improve service and retain customer fidelity Sensors used may include: EEG, heart rate (stress), galvanic (stress).

Example Application: Music Creation: Subscription Based Music Platforms

Spotify, Radio are examples of subscription based music platforms. Subscribers have access to the catalog of all music on the web site for a monthly fee. These companies can improve the accuracy of their recommendation engines by using standardized emotional responses to music. These web sites could get additional user information on their emotional state to help improve the classification. Classification of emotion can be highly variable and additional input from the user will help improve the accuracy of recommendations.

The following is an illustrative user story for this example application:

Dean is going through a rough time, emotionally.

He wants to create a playlist that will help him "power up," and approach the world with less fear and anxiety.

Dean uses Spotify with the system of the present invention to create a playlist based on his brain state.

He plays a series of songs on shuffle, and when he feels energetic and confident, the system recognizes it and tags the song with the system's emotagging system.

Eventually, the system helps Spotify build a playlist for Dean that will make him feel good.

That playlist can follow Dean anywhere that Spotify goes.

The value proposition for this user story may include:

Value Proposition: This technology allows Dean to access an emotionally-curated playlist of music anywhere he likes, via an app.

Sensors used may include: EEG.

Example Application: Express Emotion Through Music: Using EEG Information, the Emotional State of the User is Displayed to Third Parties. The Emotional State of the User is Influenced by the Music they are Listening to This example application involves using EEG information, the emotional state of the user is displayed to third parties. The emotional state of the user is influenced by the music they are listening to.

The following is an illustrative user story for this example application:

Bono is the lead singer for a popular band.

His band releases a new album. Bono invites everyone to listen to the new album during an online listening party While preparing to listen to the new album, each user wears an EEG-reading headset Each user and their EEG headset are connected to the internet. Their location is logged via IP and/or GPS (INPUT)

While the album plays, each user listens to it in sync and their emotional states (happy, sad, etc) are recorded in realtime and uploaded to the cloud (INPUT, PROCESS, OUTPUT)

Each user is assigned a pixel on a real-time map. The colour of their pixel changes according to their emotional state (OUTPUT)

Thus each listener can access a realtime map of how they and others are reacting to the song—it's a shifting colour, or "heat map". This information is shared between users via the cloud After the album is over, servers in the cloud can crunch data and provide metrics about the experience (i.e. which countries, cities or regions thought the album was "happy" or "sad; which geographical regions showed the greatest levels of "change" from one emotional state to the other, etc (PROCESS)

The value proposition for this user story may include:

Music is very closely associated with emotional responses. By collecting metrics in real time about their listener's emotional responses, musicians can learn much more about how they are perceived by their audience Sensors used may include: EEG, heart rate, skin galvanic (for emotional response), GPS.

Example Application: Express Emotion Through Music: Communicating Emotional States at a Party This example application involves communicating emotional states at a party.

The following is an illustrative user story for this example application:

Jared is a musical performer who works in a special milieu: he performs to a crowd directly through wireless headphones These headphones are equipped with EEG-sensing technology Jared performs his music; the data stream from his instruments is transmitted, either directly or via a server located on site or in the cloud (OUTPUT)

Jared's music allows people to dance together, enjoying the same music in a synchronized fashion (OUTPUT, INPUT)

The headphones worn by the dancers at the event are equipped with LEDs that are connected to the output of the EEG The headphones glow according to the brainwaves generated by the EEG. Happy emotions elicit a green glow; negative emotions a red glow, etc (PROCESS, OUTPUT)

This process thus allows both the artist and the audience members to communicate their emotional states visually to one another The value proposition for this user story may include:
Adding value to the nature of live performance by communicating the emotional state of the participants as well as the performance
Sensors used may include: microphone, EEG.

Example Application: Express Emotion Through Music: Group Musical Meditation This example application involves group musical meditation.
The following is an illustrative user story for this example application:
Jerome and a group of his friends gather for a collective musical meditation session
Each person arrives at the group wearing an EEG sensor connected to a headphone
The EEG sensors are all linked together via a central server, existing either locally in Jerome's house or remotely, accessed via the internet
The meditation session begins. Each person's EEG sensor transmits data to the server regarding their emotional state. (OUTPUT)
Emotional states are assigned a specific tone by the server (angry=A, bored=B sharp, inquisitive=C minus, etc)
The server instructs each of the headphones to play the melange of tones being generated by each of the participants (PROCESS, OUTPUT)
As each member of the group listens to the sound collage, their perception of it changes the nature of the collage, creating a kind of feedback loop (INPUT, PROCESS, OUTPUT)
As the composition of the group changes (people entering, leaving the group) or as the ambient sounds in the environment change, therefore changing the feedback pattern of the group and changing the sound collage
External sounds picked up by the microphone are capable of changing the mood dynamic of the group as well, enhancing the collage of sounds that's being produced (INPUT, PROCESS, OUTPUT)
The value proposition for this user story may include:
This process will allow us to create a new dimension in mindfulness meditation, enabling users to create their own "mindscapes" and to foster mutual cooperation
Sensors used may include: EEG, microphone.

Example Application: Express Emotion Through Music: Visualizing an Emotional Connection to an Instrument This example application involves visualizing an emotional connection to an instrument.
The following is an illustrative user story for this example application:
Spike is a famous violinist who plays a modified instrument equipped with LEDs and a wireless connection to an EEG-sensing apparatus, which Spike wears
Both the EEG sensor and Spike's violin are wirelessly linked to a server in the concert hall
As Spike plays during the concert, his emotional state is read by the EEG-sensing apparatus (INPUT)
His emotional state at each moment is read by the apparatus and is transmitted to the server (OUTPUT)
The server continually analyzes the output of the EEG device (PROCESS)
The server instructs the LEDs in the violin to change colour in response to Spike's changing emotional state (OUTPUT)
Spike can let these changes flow naturally or he can deliberately cultivate emotional states to change the colour of his violin (OUTPUT)
The value proposition for this user story may include:
Enhancing the value of musical performances by having the artist share his brain state information with the audience
Sensors used may include: EEG.

Example Application: Express Emotion Through Music: Converting Emotions into Music This example application involves converting emotions into music.
The following is an illustrative user story for this example application:
Jim and Sally are in a relationship. They own a system that consists of two EEG-sensing devices they wear when they are apart.
The EEG devices constantly measure both of their brainwave activity. The data is collected and mutually shared, either directly over the internet via their mobile devices or via a mobile server in the cloud (INPUT)
As Jim and Sally go about their activities during the day, both of them generate a continual stream of data from their EEG-sensing devices, which correlate to their emotional states and their levels of focus
These emotional states are compiled and analyzed by an algorithm residing either on their mobile devices or on a remote server accessed via the Internet (PROCESS)
As this detection process reaches maturity, both Sally and Jim will have worn their EEG-reading devices while listening to a large number of music tracks
Each track in their library will be tagged with an emotional state (i.e. "happy", "sad", etc) based on the EEG responses generated during listening (PROCESS, OUTPUT)
The more they listen, the larger and more accurate the database of tagged music becomes
Jim and Sally's emotional states are correlated to the tags on the music selections in the song libraries on their mobile devices. (PROCESS)
A continual stream of "mood-focused" music then plays based on Jim and Sally's constantly-fluctuating emotional states (OUTPUT)
Even though they may be separated by large geographical distances, either Jim or Sally can check their partner's "mood music stream" to see how the other is feeling at any given moment (OUTPUT)
The value proposition for this user story may include:
This technology will allow couples (or friends) to experience new levels of intimacy and will allow for improved harmony in their relationships
Sensors used may include: EEG.

Example Application: Behaviour Modification: Using Biofeedback to Improve Driving Performance This example application involves using biofeedback to improve driving performance.
The following is an illustrative user story for this example application:
Caleb drives many kilometres each day as part of his job (sales)

Caleb's insurance providers will offer him discounts if he stays alert and attentive while on the road Caleb likes to listen to music. He also wears brain-sensing equipment while he's on the road (a wearable computing device of the present invention or similar)

Caleb's sensors monitor his brain state while driving (INPUT)

If the detector determines that Caleb is beginning to lose focus/become drowsy, the brainwave detector will instruct Caleb's car to change the music he's listening to (PROCESS, OUTPUT). Information about which music can be accessed can be stored either on a local device in the car or in the cloud Brainwave detector monitors Caleb to ensure the new music has changed his focus/attention levels (PROCESS)

If Caleb's focus starts to drift again, brainwave sensors will detect this and change the music selection again until a stable attention pattern is achieved (PROCESS, OUTPUT)

The value proposition for this user story may include:

There are many industries (manufacturing, transportation, etc) in which a consistent level of focus is desired, especially when workers listen to music. This process will provide a consistent methodology for maintaining focus levels Sensors used may include: EEG, gyroscope (to detect head position if getting drowsy).

Another case could be to improve focus through the selection of background music. The user is given feedback on their state of focus and concentration. The user can insulate themselves from the external environment as well become aware of emotional issues that arise within themselves. The background music can be changed to help improve these factors.

GOAL: FOCUS—how much concentration and distraction—measure of how well we are doing. System tries different variations of background music. User can emphasize what they like (turn up volume)—this provides information from the user as to their preferences. User preferences can also be learned when they skip over a song therefore the system learns which songs are not suitable for focus and concentration. Also need to learn if the user turned down the volume because something else happening in their environment. Example: user is sitting at computer and being tracked with front facing camera whether user is focussing on-screen- or on the p hone. A thinking profile can also be chosen to optimize performance. The profile can be think for 5 minutes, rest for 3, think for 10 minutes etc. The background music is synchronized to the profile.

Example Application: Behaviour Modification: Biofeedback for Mindful Speech

This example application involves biofeedback for mindful speech.

The following is an illustrative user story for this example application:

Johnny wears an EEG-sensing device equipped with a microphone

The device and microphone both communicate with a computer, either in Johnny's mobile device or located on a remote server that's accessed via the Internet An app stored in Johnny's mobile device records Johnny's voice and his emotional state (as captured by the EEG device)

The app creates correlations between his brain state and his vocal tone

As Johnny uses the app more and more it becomes able to predict his vocal tone based on his brain state The app will alert Johnny, either through audio feedback or through a vibrating mechanism, when his current speech may not be received as he intends it to be Based on this new level of awareness, Johnny can choose to alter his speech patterns or, alternatively, he can choose not to speak at all—depending on his current context Johnny's EEG sensor can be connected directly, either via the internet or via the cloud—to another individual's EEG sensor, which is also connected to an app running on that person's mobile device, or which is resident on a server accessed via the internet This connection facilitates Johnny's emotional state directly to the other user so the other user can best judge Johnny's emotional state with as little confusion involved in the process as possible The value proposition for this user story may include:

Creates stability for individuals with poor affect judgment (Asperger's spectrum, etc or autism) that will enable them to be better judges of other people's emotions. Can serve as a valuable therapeutic tool Sensors used may include: EEG, microphone.

As another example, Johnny and Brenda tend to have heated arguments at work, so they hire a conflict resolution expert who uses EEG-sensing devices equipped with a microphones Johnny and Brenda wear the devices which both communicate with a computer setup where both people can see a display of each other's state.

After calibrating, Johnny and Brenda are asked to discuss a sensitive topic, and the devices record their voice and emotional states (as captured by the EEG device).

The application creates correlations between brain state and his vocal tone and displays their emotional states during the discussion to the other speaker.

The application alerts Johnny and Brenda in real-time, either through audio or visual feedback, when their current speech may not be received as they intend it to be.

Based on this exercise, Johnny and Brenda learn to alter their speech patterns and when not to speak at all—depending on each other's emotional state.

This exercise facilitates a better work relationship between Johnny and Brenda by training them to recognize each other's emotional states emotional and learn to be more mindful of their actions and speech when working with each other. judge The value proposition for this system architecture may include many other use cases: individuals with poor affect judgment (Asperger's, autism) that may enable them to be better judges of other people's emotions. This may serve as a valuable therapeutic tool. Further example may be preparing for a presentation or speech with a direct read on audience emotional states and using that to improve the presentation/speech.

Sensors used may include: EEG, microphone.

Example Application: Using Music to Change Your Mood: Using Music to Change Your Mood (MR)

This example application involves using music to change your mood.

The following is an illustrative user story for this example application:

Helo wants to improve his mental state, to become "cheerier"

Helo instructs his mobile device that he wants to change his mood to something more positive The mobile device responds, initially, by playing a random selection of tracks. The music data is either stored locally on Helo's device or is streamed via the Internet An EEG-measuring device (e.g. the wearable computing device of the present invention) keeps track of Helo's emotional state while listening to the music selection A shift towards a positive emotional state is tracked by the EEG device. Helo's mobile device records the song as being "emotionally positive"

Over time, the EEG device builds a profile of "positive songs" based on EEG measurements. This "mood data" will be stored locally on Helo's device but for analysis it can be sent to the cloud Additional indicators of positive mood may be motion-based (dancing) or increased heart rate (excitement)

As Helo plays more songs the algorithm that determines whether a song is "positive" becomes more and more accurate. Similar to Google Translate, the analytics can be performed on the cloud After a while the mobile device will automatically play "positive songs"

The EEG reader (and/or other sensors) will continually check the validity of the algorithm's predictions in case Helo's response to the songs change The value proposition for this user story may include:

Improvement of emotional states is a huge market (brain training apps like Lumosity, etc). EEG-based monitoring of how music affects mood will be a valuable tool to exploit this market since music and emotional states are closely correlated Sensors used may include: EEG, heart rate, stress (galvanic), motion (gyroscopic).

Example Application: Therapeutics: Using Music and Brain Scan Technology to Aid in Injury Recovery This example application involves using music and brain scan technology to aid in injury recovery.

The following is an illustrative user story for this example application:

Phil has sustained severe injuries to his right leg in a car accident

To regain the use of his leg, Phil undergoes a few hours of intensive physiotherapy each day while wearing a brainwave scanning device Phil likes to listen to different types of music while he works on his recovery, including classical, jazz and rock Each of these different types of music affects Phil's mental state in a different way. The physiotherapy staff monitors these changes because they want to optimize Phil's recovery Throughout Phil's treatment, a profile of how he responds to each type of music is recorded by a computer For example: jazz relaxes him; rock energizes him; classical improves his level of focus As Phil is exercising, his brain state is monitored by the clinic's staff The clinic staff change the type of music to match the desired treatment outcome i.e.: if they want Phil to be relaxed, jazz is played; if they want to improve focus, classical music is played If Phil's responses to the music change over time, these changes are logged by the computer and treatment options are varied accordingly The value proposition for this user story may include:

Therapeutic treatment options for a variety of conditions are as varied as the people who are seeking therapy. Music is a well-documented therapeutic tool. By tracking specifically how different people respond to different types of music a highly-personalized, individual treatment profile can be generated that changes according to the therapeutic outcome.

Sensors used may include: Brainwave, stress (galvanic response), body temperature, movement (gyroscope).

Example Application: Therapeutics: Musical Psychotherapists

Use music for emotional healing. They can improve their practice by obtaining more objective emotional data in terms of before, during and after playing of music. The therapist can more quickly determine which music selections are having the biggest impact on their patients.

Music therapy typically comprises of an a therapist and a patient or group of patients. Patient plays music on instruments and non-instruments alike to gain emotional contact with his internal experience. The therapist is there to guide him, hold space, or talk about the insights and experiences that arise for the patient. In EEG enabled Musical therapy, the music can be made directly from a patients EEG activity. For example, brain input can go into a midi or other musical controller such that brain activity maps to sound creation. For example low frequency brainwaves can be mapped with low frequency sounds, and high frequency brainwaves can be interpreted to produce high frequency sounds. Or brain activity can control an aspect of the sound, like pitch or volume. Lighting can also be mapped to brain state and co-vary.

A group of patients can each play music created with their own brain state, and play in concert with one another. For example, when the players synchronise brainwaves, new effects in the music can be created.

The therapist can play alongside the patient as well. For example with reward when the patient and therapist are in synch with their brain activity, for example they could be in phase, cohere, or same frequency.

Rapport between patient and therapist has been known to be highly beneficial to the therapy. Also, an EEG system could detect the mood of a patient, via their brain activity. Sound could be mapped to mood, so the patient can "hear" their changing moods, or work with sound to alter mood. For a simple example a sad mood could be mapped to low sounds, and a happy mood to high sounds, and patient would practice changing mood by changing sound.

Example Application: Therapeutics: Detection of Brain Events Using EEG Technology This example application involves detection of brain events using EEG technology.

The following is an illustrative user story for this example application:

Jenny works as a neuroscientist in a hospital. She uses EEG-sensing technology to obtain new therapeutic outcomes for her patients Jenny applies EEG sensors to her patients to obtain neurological indicators of their brain health These recordings take the form of a "brain album"—they consist of EEG recordings of various neurological conditions, such as stroke, seizure or migraine (INPUT, PROCESS)

Jenny or her institution develop an app that can be downloaded by patients with various brain disorders This app can be run continuously by patients. By using this program, patients can "hear" when they are likely to experience a traumatic brain event, such as a seizure or a stroke (OUTPUT)

This information is transmitted to them via a unique auditory signature through a pair of headphones. Each "brain event", such as a stroke or seizure, is correlated to a specific auditory signal (PROCESS, OUTPUT)

When negative brain events are not occurring, Jenny's patients can listen to music that they enjoy. But the EEG-based "early warning system" is continually monitoring their brain activity to sense the presence of oncoming negative brain events. (PROCESS)

The value proposition for this user story may include:

Neurological disorders are common and place a large economic and social burden on society. In addition, detecting brain trauma early is a key method to reduce the destructive impact of the events. By deploying EEG technology, early detection of negative brain events can be improved Sensors used may include: EEG.

Example Application: Therapeutics: Detection and Enhancement of ASMR (Autonomous Sensory Meridian Response)

This example application involves detection and enhancement of ASMR (autonomous sensory meridian response).

The following is an illustrative user story for this example application:

Laura is an individual who experiences ASMR. This means she experiences a "tingling" sensation along the spinal column when she hears particular sounds Examples of sounds that trigger this sensation include whispering, clicking, crinkling of soft materials, lip-smacking or breathing Laura downloads an app onto her mobile device that is connected wirelessly to an EEG-sensing device that she wears. Laura also wears a microphone The app is programmed with information that conveys that Laura enjoys the ASMR experience—she finds ASMR trigger sounds calming and soothing (PROCESS)

When the app is running, it listens to Laura's ambient environment continuously (INPUT, PROCESS)

In the process of listening, the app assists Laura in finding people in her environment who will stimulate the ASMR experience This stimulation is based on patterns of speech; accents; volume levels of voices (INPUT, PROCESS)

When the app detects a sound pattern that is likely to trigger an ASMR response in Laura's general environment, the app responds by "turning up the volume" on that particular individual (INPUT, PROCESS, OUTPUT)

The result is that even though the ASMR-triggering sounds may be quiet in the general environment, they sound loud and clear to Laura The value proposition for this user story may include:

ASMR is a therapeutic process that makes people relaxed and provides comfort. An app that specifically selects sounds that are likely to induce this response has therapeutic value Sensors used may include: EEG; microphone; galvanic skin response (to detect "tingling" when ASMR response is achieved.

Example Application: Therapeutics: Depression Amelioration Through Positive Brainwave Reinforcement This example application involves depression amelioration through positive brainwave reinforcement.

The following is an illustrative user story for this example application:

Joseph suffers from depression

He wears an EEG-measuring device as well as a headphone

He has an app loaded onto his mobile device that detects his brainwave activity while he listens to music (INPUT, PROCESS)

This app is designed to sense alpha waves—a signifier of positive mental health (PROCESS)

As Joseph listens to music on his mobile device, the app interfaces with his EEG-sensing device, scanning his brainwaves for the presence of alpha waves (INPUT, PROCESS)

Over time, as Joseph listens to more and more music, the app on his mobile device will be able to detect which songs are capable of inducing alpha waves (PROCESS)

The more music Joseph listens to on his mobile device, the more accurate the profile of his alpha-wave-inducing playlist becomes (INPUT, PROCESS)

Joseph listens to songs tagged with alpha-wave inducing properties to boost his mood when he's feeling low (OUTPUT)

Joseph's headphones are equipped with bright LEDs in close proximity to the ears The lights glow when Joseph is listening to his alpha-boosting playlist (OUTPUT)

Research suggests that shining light into the ears can increase serotonin levels (associated with depression amelioration) after 8 minutes of exposure The value proposition for this user story may include:

Listening to music is a proven method to help people tackle depression. The methodology described above can maximize the benefits of music-based therapy by using specific songs that are shown to have a therapeutic benefit Sensors used may include: EEG, microphone.

Example Application: Therapeutics: Assistance for the Blind Using EEG Technology This example application involves assistance for the blind using EEG technology.

The following is an illustrative user story for this example application:

Ray is blind

He is afraid that he will miss key emotional cues from other people because of his lack of sight He is also concerned that people he speaks to (doctors, nurses, service staff) don't listen to him as well as they should As part of his care regimen, people who frequently associate with Ray are encouraged to wear EEG-sensing devices Ray wears an EEG-sensing device too, as well as a headphone The outputs from the EEG-sensing devices from the people who are around Ray are transmitted into Ray's mobile device, either directly, or through a remote server accessed via the Internet (INPUT)

Using an app installed on his mobile device, Ray is able to hear changes in the brain state of the people who surround him (PROCESS, OUTPUT)

The changes in brain state are interpreted by the app running on his mobile device as a series of tones (OUTPUT)

When the people who surround Ray have their brain state change when Ray is talking to them, a tone will play in Ray's headset allowing him to detect when the change occurs (PROCESS, OUTPUT)

In addition to EEG-sensing devices, the people who surround Ray can also be compelled to wear additional sensors that track changes in mood (such as heart rate and eye track). When these sensors pick up changes that vary from baseline, Ray will hear a musical tone in his headphones The value proposition for this user story may include:

The implementation of this technology will allow blind and visually-impaired people to participate more in the cultural milieu that surrounds them. They will be able to feel more empowered, less ignored and can have more meaningful conversations with their caregivers. The same technology could be used to improve the lives of people suffering from prosopagnosia (face blindness) or autism spectrum disorders Sensors used may include: EEG; heart rate; eye track; galvanic skin response.

Example Application: Therapeutics: Support of Brain States Conducive to Sleep

This example application involves support of brain states conducive to sleep.

The following is an illustrative user story for this example application:

Billy puts an EEG-sensing device before going to sleep at night

Billy's mobile device plays music (OUTPUT)

The EEG-sensing device tracks Billy's brainwave activity while he listens to music in bed (INPUT, PROCESS)

An app installed on Billy's mobile device tracks Billy's sleep patterns as he listens to the music tracks on his mobile device (PROCESS)

Songs that induce restful sleep are tagged on his device as being useful for sleep (PROCESS)

The more Billy listens to music on his device, the more accurately the app can predict which songs are likely to induce sleep, based on EEG-derived information (PROCESS)

A feedback mechanism is enabled which allows the system to evolve to match Billy's preferences as they change as he listens to more and more music (PROCESS)

As the music plays while Billy is in bed, the EEG device is monitoring his brain state and delivering that information to the app on his mobile device (INPUT, PROCESS)

When the EEG device detects that Billy is approaching a sleep state, the app automatically fades the music volume down (PROCESS, OUTPUT)

When the EEG device detects that Billy has fallen asleep, the app on his device fades out the music entirely (PROCESS, OUTPUT)

If Billy wakes up at any point during the night, the EEG device will detect this change and music that supports sleep will begin to play again (PROCESS, OUTPUT)

This process will repeat in a loop as many times as is necessary for Billy to sleep peacefully throughout the night (PROCESS, OUTPUT)

The value proposition for this user story may include:

Insomnia and sleep disorders are a significant health problem for a significant percentage of the population. A drug-free way to remedy the problem has significant market potential Sensors used may include: EEG.

As another example, a user may be playing music during the day time to train sleep at night. As an illustration, one plays Music containing 13-15 hz sounds. 13-15 hz is the frequency of sleep spindles, they arise during stage 2 sleep and indicate the onset of sleep. Research has shown that training sleep spindles from areas including the sensory motor cortex during the day leads to improved sleep latency, and also improved declarative memory the next day. The user can listen to Music that contains 13-15 hz binaural beats to entrain the brain. The user can listen to music and be wearing an EEG with sensors at, for example c3 and c4 (in 10-20 system), and when the user produces a 13-15 hz frequency the music will adjust as a reward for the listener, thereby entraining 13-15 hz spindles.

Example Application: Assessment of Human Emotional Response to Music: Emotional Appraisal Using Stimuli The following is an illustrative user story for this example application:

Sigmund is a member of the Canadian Armed Forces. He applies for a promotion, and is introduced to Dr. Jones.

Many people who have PTSD will have triggers such as certain sights, sounds, or smells often around the anniversary of the trauma—See more at: http://www.band-backtogether.com/ptsd-resources/#sthash.tekWKE6E.dpuf Dr. Jones wants to do a psychological assessment of Sigmund as part of the interview process for the promotion, which will require a cool head in high-stress situations, and split-second decision-making. Dr. Jones is concerned that Sigmund's experience in Afghanistan has led to PTSD. If it has, and if Sigmund earns the promotion, Dr. Jones will need to help Sigmund manage his condition so that he can be an effective leader and communicator.

Dr. Jones fits Sigmund with a brain-sensing wearable computing device of the present invention or suite of devices.

The assessment consists of listening to certain sounds in the headphones of the wearable computing device while brainwaves are read by the device(s). Dr. Jones needs to understand Sigmund's response to that audio stimulation, as a means of understanding how he will react in specific situations. The stimuli involves loud noises, loud music, voices talking over each other, raised voices, and other common audio triggers to patients with PTSD.

As Sigmund experiences the stimuli, Dr. Jones watches how Sigmund's brain responds via the wearable computing device. Dr. Jones takes note of eye-tracking (EOG) and Steady-State responses to stimuli to work up a diagnosis.

After the assessment, Jones is provided with an assessment report detailing Sigmund's emotional responses to the various stimuli and what that means about his emotional state and intelligence.

The value proposition for this user story may include:
The system of the present invention offers users access to real-time data on emotional and psychological responses to audio stimuli.

Sensors used may include: emotional responses detected in real-time while user engages with stimuli.

Applications may include: Therapy, on-the-job assessment, testing, academic/pedagogical, mental health arena, testing for specific.

Example Application: Machine Maintenance: Funny Car Sounds Alerts Mechanic

The following is an illustrative user story for this example application:

Wendy is wearing a wearable computing device of the present invention. She is driving down the highway when all of a sudden her car starts making a funny sound. Brainwave sensors pick up the salient P300. This informs the car's onboard computer to log the associated engine measures with the perceived sound. The sound may be intermittent.

Wendy's mechanic can be alerted and auto manufacturers can use the knowledge to improve diagnostics and automobile performance.

The value proposition for this user story may include:
improved ability to diagnose intermittent and or persistent sounds. Early warning of changes in sound characteristics that can prevent expensive auto repairs.

Sensors used may include: auto sensors; EEG sensors.

Example Application: Filtering of Content: Ad Blocker

The following is an illustrative user story for this example application:

Fred is listening to the radio via his wearable computing device(s) of the present invention when his reverie is disturbed by an annoying ad. Fred is interested in some ads, but there are others that he prefers to ignore.

The system of the present invention has a context-dependent Brain State profile of how Fred's brain reacts to regular stimuli as a baseline. When Fred doesn't like something, he registers a negative reaction via the system.

The system pattern-matches Fred's response against the specific ads that Fred was hearing at the time.

The system of the present invention filters out the ads that Fred prefers not to hear.

The value proposition for this user story may include:
This technology allows users to dictate which ads they hear, and provides advertises with rich data on what ads they like, as well as how their brains respond to each ad. Eventually, this leads to better, more enjoyable advertising that people actually enjoy listening to.

Sensors used may include: microphones, EEG.
Applications may include: radio, television, and web.

Example Application: Filtering of Content: Selective Eavesdropping

The following is an illustrative user story for this example application:

Winona is in a cafe wearing a wearable computing device of the present invention or suite of devices. It can sense brainwaves and can focus microphones to tune in a sound in frequency and direction.

She hears a speaker (or a voice, or a sound) over the din that her brainwave sensors detect as being pleasant. Her headphones begin tuning in the listener and Winona P300 response is used to bring the target of her attention into focus so she can listen in selectively to a conversation.

Depending on Winona's responses and her contextual baseline Brain State, Winona can choose to filter out the sounds that she doesn't like. Or she can make sure that she doesn't hear conversations that she has no interest in.

The value proposition for this user story may include:
People in public spaces don't always remember that their conversations can be overheard. This would give their neighbours the opportunity to screen out their conversations, or "listen closer" if the conversation is really good.

Sensors used may include: EEG, microphones, baffles that guide and channel sound.

Applications may include: Gossip blogging, social networking, interviews, journalism.

Example Application: Filtering of Content: Selective Hearing (L3)

The following is an illustrative user story for this example application:

Dick literally never listens to Jane.

Dick programs the system of the present invention to listen for when Jane is angry, based on her blood pressure, temperature, and other available inputs, available from Jane's freely-shared system data.

Dick programs the system to play white noise over Jane when she's angry. Dick doesn't hear her anger.

Their relationship finally snaps when Jane realizes he's been using the system to literally tune her out.

The value proposition for this user story may include:
The ability to tune out the things or people who cause us distress is a double-edged sword. On the one hand, we can avoid hearing things like hate speech, or curse words, or bullying comments that undermine our sense of self. On the other hand, we could literally tune out the people around us. Depending on what the user wants, this can go a variety of ways.

Sensors used may include: Skin temperature, blood pressure, frontal lobe sensors.

Applications may include: Mediation, negotiation, avoiding "triggering" conversations, screening out angry people in a customer service or public service context (angry people in line at the DMV, etc.).

Example Application: Filtering of Content: Whispering Gallery

The following is an illustrative user story for this example application:
- Alex is slowly losing her hearing. She has trouble discerning one person's voice from another's in a crowd. Unfortunately, she works as a journalist at City Hall and often needs to pay close attention during press conferences and scrums with the Mayor, when things can get noisy.
- Alex purchases the wearable computing device of the present invention to help her filter out the sounds she doesn't want to hear.
- Alex spends time listening to specific sounds, and the system of the present invention reads her reactions to understand the things she doesn't want to hear (like the sound of a camera shutter, for example, or the sound of someone else's text messages arriving).
- Alex also practises with the system to understand whose voices she should be hearing during a scrum. The system uses microphones to record entire press conferences, but screens out other reporters' voices so that Alex can concentrate. This way, she can re-play the entire conference if she wants to, but she doesn't feel the same stress and frustration that she used to during a press conference.
- The value proposition for this user story may include:
- This technology would enable the hearing-impaired to listen only to what they needed to hear, while also recording an entire conversation that they might otherwise have missed. Similar to real "whispering galleries": http://en.wikipedia.org/wiki/Whispering_gallery Sensors used may include: Microphones, gyroscopes, motion detection.

Applications may include:
Noisy environments, press galleries, crowded environments.

Example Application: Filtering of Content: Personal Channels/Brainwave as Tuner/the Sound of Long Distance Relationships (L3)

The following is an illustrative user story for this example application:
- Audrey is in a long-distance relationship with Humphrey. She lives on the West Coast, and he lives on the East Coast.
- One of the ways the two of them stay connected is for each of them to "tune in" to the sounds that each of them enjoys hearing in their local environments. For example, Audrey likes to hear the sound of the native birds in Humphrey's neighbourhood when he wakes up, even though he wakes up three hours ahead of her.
- The system of the present invention logs when Humphrey wakes up by analyzing and interpreting his brainwaves, and begins recording the sounds that Humphrey is hearing.
- The system logs the sounds that Humphrey appears to enjoy. It takes note of his brainwave responses and also measures the movements of muscles in his face and where his eyes go, via eye-tracking.
- When Humphrey listens closely to a sound, the device "learns" his response and begins recording the sound.
- Each day, the sounds are sent to Audrey's wearable computing device of the present invention. Audrey sets a default in the headphones to make sure that these sounds are her wake-up alarm. Each morning, Audrey hears the sounds that Humphrey heard upon waking, when she wakes up.
- The value proposition for this user story may include:
- Finding out what sounds people focus on during the day is important to understanding emotion, productivity, perception, and intelligence. With information like this, people can grow closer and understand each other better using raw data, rather than interpretation.

Sensors used may include: Microphones, eye-tracking, sensory strip, galvanic muscle response.

Applications may include: Long distance relationships, surveillance, eavesdropping, journalism.

Example Application: Social Networking Through Musical Preferences: Sharing the Same Tastes in Music Finding out the music that someone else likes seems to give you a lot of information about them quickly. For example, college students getting to know each other over the internet may be more likely to ask about music preferences than about all other categories of conversation topics combined. Further, knowing someone's music preferences may allow students to do a reasonable job of predicting some of the new person's personality characteristics and values. Unsurprisingly, people expressed that they liked a new person better when finding that they shared the same musical taste than when they did not.

This example application involves sharing the same tastes in music.

The following is an illustrative user story for this example application:
- Finding a partner online is a difficult task because of how easy it is for one to create a persona that is not truly representative of their personality. What is necessary are more honest online personae, with real information on a person's tastes.
- Darla goes on-line to a dating web site. She is worried about "being herself," but she's also ready to get serious with her online dating profile.
- While wearing a wearable computing device of the present invention, she listens to music that is selected by the dating web site to be representative of certain genres. She listens to tunes she has never heard before, as well as old favourites. She listens to multiple genres, some of which she never really listens to and others which she hasn't listened to in quite some time.
- The system of the present invention records all her Brain State responses to the music, brainwaves detected from the auditory cortex, pre-frontal cortex and other parts of the brain involved in processing and creating emotional responses to music. In addition motion detection, and eye-tracking are analyzed to determine if the user is dancing or moving to the music adding additional evidence that she is having an emotional response to the music.
- The system records and stores her preferences of music based on frequency of song choice, dancing, and Brain State.
- This generates an Output that is much like a Profile. The Profile has all her music preferences (even the ones she's not consciously aware of, like songs she enjoys but hasn't purchased yet).
- Her Profile is used to match to the preferences of other daters on the web site.

The value proposition for this user story may include:
The system can capture people's authentic reaction to music. Taste in music is often an important predictor and selection criterion for people looking for a partner.
Sensors used may include: brainwave sensing headband.
Applications may include: Online dating, music promotion, music label/A&R promotion.

Example Application: Social Networking Through Musical Preferences: Musical Genre Definition Through Emotion This example application involves genres of emotion
The following is an illustrative user story for this example application:
Blingo is a music executive who is about to release a new artist.
Blingo doesn't know exactly how to determine the genre of this new experimental music; he just knows that he wants to promote it and help it find the right audience who will appreciate it.
Lucky for Blingo, traditional genres are a thing of the past. Thanks to the end of radio, musical artists are less about genre and more about branding. He just needs to develop this artist as a brand and hope that brand finds an audience.
Blingo submits a track to an online service which introduces the song to a group of 1000 listeners online. These listeners are also wearable computing device of the present invention users. The service grants them access to music before it's released publicly, on the condition that they use their devices to listen to the music and agree to have their responses recorded for marketing and research purposes.
Those 1000 people listen to the song in a neutral environment when they're in a self-assessed neutral mood, and the effects it has on their emotions, Brain State, and physical well-being is recorded via the system of the present invention.
The emotional affect data is summarized and analyzed to create an emotional profile for the music.
This emotional profile defines the song's genre.
Blingo is satisfied after his busy day, and pops on a playlist at home. He sets the playlist to sort by genre, where he chooses "Wind-down"—the songs on this playlist have all been shown to have a calming effect on the human mind.
"Emoshift"—Emotional Shifting of Piece of Music
Definition: A rapid shift from one emotional state to another. Emoshift can be accomplished by listening to music. We try to create an emoshift or other times we want to catch emoshifts. Have meta-awareness of the shift and therefore transform undesirable emotions into positive attitude.
Artist—can track emoshifts in users to get feedback on the creative process.
User—Wants to change their mood and can use music to archive the emoshift.
Advertisers want to understand how to use emoshift to influence their audience. Advertisers can identify users that respond to the music they include.
Emoshift Target—Specific goal of changing mood. Key change—elevating tenor—famous key changes—moment song shifts key change.
The value proposition for this user story may include:
This service would allow listeners to help define the impact of music on their Brain States, and help them learn more about the sounds and pieces of music that have beneficial (or negative) effects on them as individuals.
Sensors used may include: Detecting emotional state of diverse users listening to a single song, and transmitting that data remotely. Analysis of that data to produce an "emotional effect" that it has on people.
Applications may include: Promotion, marketing, market research.

Example Application: Social Networking Through Musical Preferences: Choose Your Own Adventure Pop Music Phrases This example application involves choose your own adventure.
The following is an illustrative user story for this example application:
Pearl is a pop music producer.
Her craft is to create punchy, catchy songs which capture the hearts of millions.
In order to increase engagement with her pop songs, she decides to leverage the fact that many people listen to music while wearing brainwave sensors in their wearable computing devices of the present invention.
The artist Pearl is working with has a clear dichotomy in his fan base. Some take him really seriously and love to hear his soulful side, while others just see him as a party animal.
Pearl decides to build on this by creating two different endings to his latest song.
When listener brainwave data is available, the song analyzes that data and determines the listener's response to the song.
When the listener is excited and engaged by the rhythm of the music, the song automatically plays the upbeat dance-party ending to the song.
When the listener seems more verbally engaged, listening to the lyrics and connecting with the songwriter, the more soulful ballad-esque ending plays.
The value proposition for this user story may include:
This technology would allow listeners to "emotionally re-mix" the song that they are listening to. Depending on how they're feeling, a song might turn out a different way, or take on a different key. They can choose to "fade out" a song, or end it with a bang. This provides a soundtrack to everyday life. This technology would also allow music listeners to learn more about the emotional effects of music—music teachers could use it in the classroom or in a tutoring context to help students learn about how they and their classmates respond to music on an emotional level, all while experimenting with that music.
Sensors used may include: Brainwave sensors, motion detectors, gyroscopes.
Applications may include: Social networking, apps, music composition, music education.

Example Application: Social Networking Through Musical Preferences: Social Networking Appreciation of Music This example application involves a Speakeasy with Music as Gathering Space/Band Together.
The following is an illustrative user story for this example application:
Billus loves music, and has a vast collection of old and rare music recordings from artists many of his peers haven't heard of.

Billus listens to his music on a random shuffle setting, and when a particular track comes on, his wearable computing device of the present invention detects his nostalgia and deep emotional reaction using a future function of the device, while simultaneously recognizing the song through its built-in microphone.

The nature of the emotional moment Billus has sends him access to a special web forum around that particular song.

This entry only happens when a person brainwaves are classified into a specific type of emotion and level of emotion. The curator of the group decides on the level and type of emotion she/he is willing to join this group.

When he accesses that web portal, he's able to see lively discussions and other content generated by fellow music lovers who all love that same song/artist/album/etc.

The artist of that song is much older now, but has provided some special content on the page, which is only accessible here.

Every single person on that web forum by definition has had a similar genuine emotional response to the same piece of music, that's how it allowed them all to access the forum.

The forum is off limits if you have not had this response.

The value proposition for this user story may include:

People have always gathered around music. Whether it's spiritual or social, music creates a gathering space. Most major social movements also have a musical aesthetic associated with them—for example, the Jazz Age is inextricably linked with innovations in the art of popular music. At all points in history, people have banded together through music.

Consider the moment in Garden State when Natalie Portman's character introduces herself to the film's protagonist by putting a pair of headphones on his head and sharing her favourite song by The Shins with him. This technology would help facilitate that interaction.

Figure 7:
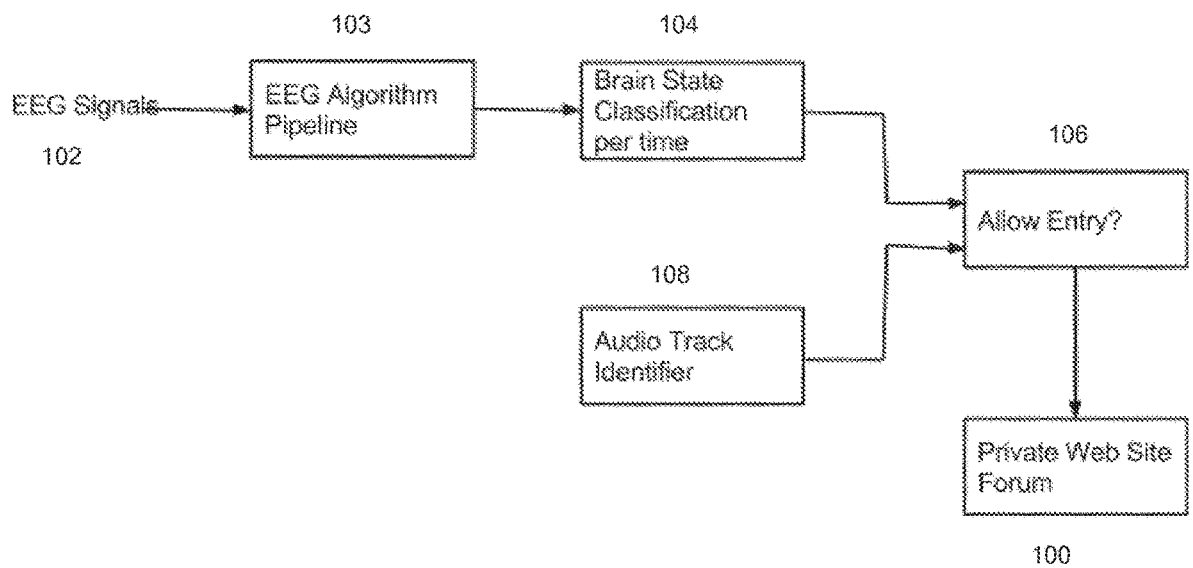
FIG. 7 illustrates an exemplary architecture of the present invention in accordance with an aspect of the embodiments described herein.

FIG. 7 shows an exemplary system implementation of the present invention for implementing this user story. In this architecture, the EEG signals 102 of the user are classified (via EEG algorithm pipeline 103 and Brain State Classifier 104) while listening to a specific audio track of an artist. The audio has a unique identifier 108. There is a Private Web Site 100 that is run by a moderator. The moderator 106 decides which brain states and the strength of the brain state to allow new users into a private forum where people can share their feelings and thoughts about the audio track.

Example Application: Social Networking Through Musical Preferences: Asynchronous Merging of all Listener Data This example application involves asynchronous merging of all listener data.

The following is an illustrative user story for this example application:

Johnny logs on to a new website which offers him a chance to listen to his music in new ways.

He finds an interface which asks him to input a song he wants to explore.

Johnny decides to pick his favourite song, "Believe" by Justin Bieber.

Johnny is confronted with metrics for the song based on people's neural responses to the song over time, generated from aggregate data on contextual baseline Brain State established by wearable computing devices of the present invention.

The metrics can give him a different sense of what is enjoyable about the song, and how other people respond to it.

He finds other people who started dancing in their chairs at the exact second that he did while listening to the song, and realizes he's not so ridiculous for liking Justin Bieber (or any major pop artist).

The value proposition for this user story may include:

This service would allow listeners to learn whether their response to a song is distinctive, or whether they share that same reaction with other listeners at the Brain State level. This helps concretize the deeper connection that some people feel to specific songs.

Sensors used may include: Brainwave sensors (bone conduction).

Applications may include: Marketing, promotion, music engineering, sound engineering, social networking.

Example Application: Social Networking Through Musical Preferences: Facebook My Musical Emotion (L1)

This example application involves Facebook (or other social network platform) with a My Musical Emotion (L1).

The following is an illustrative user story for this example application:

D'Angelo is feeling sad because he failed his driving test.

He is also wearing a wearable computing device of the present invention.

The system of the present invention uses available sensors to detect a change his mood from contextual baseline.

Based on his individual user settings, the device offers to play song to match his perceived mood.

D'Angelo agrees, song starts to play

The system updates his social media profiles with news about his mood and his song choice.

The value proposition for this user story may include:

This technology adds layers of meaning and connection to existing social media content, based primarily on musical taste and mood detection.

Sensors used may include: Bone conduction.

Applications may include: Music retailing, social media, listening to music at home; at work.

Example Application: Social Networking Through Musical Preferences: Emotional Tagging (L1)

This example application involves emotional tagging (L1) or content enhancing.

The following is an illustrative user story for this example application:

Bree is listening to a song on her mobile device.

She has technology of the system of the present invention attached to that mobile device, either via an app or a separate wearable device.

The system scans Bree as she listens to her music.

Differentiating changes in her Brain State, indicates Bree is very relaxed.

According to her individual user privacy settings and with her permission, Bree's mobile device posts the song's title on Bree's Facebook or other social network wall, along with emotional state (Bree is relaxed right now).

The value proposition for this user story may include:
Music and emotions are closely linked. People may want to purchase music that corresponds to their emotional states.

Sensors used may include: Bone conduction, eye-tracking, heart-rate.

Applications may include: Social media sharing, marketing.

Example Application: Social Networking Through Musical Preferences: Audience Measurement (L1)

This example application involves audience measurement.

The following is an illustrative user story for this example application:
The Shondells have a new album that's set to come out soon. They want to have a party to celebrate. The audience at the party is equipped with brainwave sensing technology of the system of the present invention.

Changes in contextual baseline brain state are recorded during the performance. Changes in contextual baseline brain state can also be fed back to to Shondells in real-time illustrating audiences relative involvement in their musical pieces. Shondells adapt their musical creation in real-time to connect in a desired way with audience members. Marketing of the album is tailored to the emotional response and aggregated data.

The value proposition for this user story may include:
A new kind of "focus grouping" based on brain scan metrics. This would be a standardized metric to a person's emotional response to music, entertainment, etc. People's internal mood and thought state is next to impossible to interpret. A new kind of way to "intuit" the moods and state of individuals in real-time can provide information to adapt our response and approach in real-time based on their personal data.

Sensors used may include: Bone conduction, galvanic skin response, temperature, gyroscope, accelerometer.

Applications may include: Marketing movies, music, TV shows, etc.

Example Application: Social Networking Through Musical Preferences: Sound Collage (L1)

This example application involves a sound collage.

The following is an illustrative user story for this example application:
Jackson wears his wearable computing device of the present invention on a regular basis, most of the day almost every day. It monitors his brainwaves and every sound he hears (although it does not record them).
Over time it learns to correlate his emotions to particular sounds that he hears.
Later, when Jackson is really frustrated, he wants to share it on his favorite social media site.
He types a status update into the social media app and presses a button on his phone.
The system checks the last few minutes of his brainwave recording for any significant emotional events.
The system identifies frustration as the most prominent emotion.
The system then combs through the audio recordings of Jackson's life, and looks for sounds that are correlated with similar levels of frustration.
The system assembles a sound collage of frustrating sounds.
When Jackson's friends click on the status update in their newsfeed, they hear the sound collage.

The value proposition for this user story may include:
This functionality correlates specific sounds with specific emotions. The system of the present invention allows the detection of this relationship between stimuli and response. It also encourages users to create sound "collages" or "mixes" of sounds that make them feel a certain way.

Sensors used may include: microphones, brain sensors.

Applications may include: social media.

Example Application: Social Networking Through Musical Preferences: Emotional Data-Mining of Public Spaces The following is an illustrative user story for this example application:
Trent is designing an opera house and performance space.
Trent wants to know how visitors to his space will feel in it.
Working with a design research team, he accumulates data on 100 people visiting performance spaces similar to the one he intends to build.
The people in this sample are all wearing wearable computing devices of the present invention when they attend concerts, lectures, films, or other performances.
The system of the present invention logs specific changes to their Brain State and begins recording or "listening" when those changes occur.
Eventually, the system generates aggregate data on sound quality within a performance space, and how visitors react to sound quality.
For example, some users might feel mildly annoyed at poor sound quality, but not feel compelled to leave the space. Others might not like how far away from the stage they are, but appreciate the quality of the sound.

The value proposition for this user story may include:
For example, this may be central to what the system is capable of doing. What the system does is harvest Brain State data in context. It registers changes in Brain State and interprets the wearer's emotions based on those changes to contextual baseline.
Learn how people feel about the sound of a space. Apply these learnings to a building, space, game etc.

Applications may include: Architecture and urban design, design of spaces dependent on sounds like sports stadiums and major performance venues.

Example Application: Social Networking Through Musical Preferences: Emotional Arena An emotional arena is a physical or virtual space that is engineered to promote a certain emotional state among people in the arena. Emotional Arena can be for entertainment, but it's also an opportunity to create an experience unlike any other previously available.

The following is an illustrative user story for this example application:
Frances is an architect. She is creating a new shopping mall.
Frances wants to know how sound will influence shoppers.

Working with sample shoppers in malls she wants to emulate, Frances asks her sample to wear the wearable computing device of the present invention while going shopping.

Frances is interested in how shoppers listen to or ignore announcements over loudspeakers, and how she can speed up crowds of people using music or sound.

The statistical sample wears the wearable computing device while they go shopping.

The system of the present invention takes note of their emotional reactions to auditory stimuli.

The system then maps these data points against location and sales data within the store. (Where was the shopper? What was on sale? How many people were around them? Had they just heard an announcement?)

The system generates data on these reactions and sends it to Frances.

Eventually, Frances is able to design environments that allow for a free flow of people, but still facilitate retail sales.

Sensors used may include: Cameras, microphones, bone conduction (EEG).

Applications may include: Theme park design, experience design, experience prototyping, architecture, urban planning and design, museum and exhibit design, outdoor design.

Example Application: Improve Performance: Dance Games with Head Movements (L1)

This example application involves dance games with head movements (L1).

The following is an illustrative user story for this example application:

Roc is the master of games like Dance Dance Revolution, and other games that require the player to dance based on visual and audio prompts. Roc is very competitive with these games and participates in online and arcade guilds.

He wants to improve his skills at these games, so he buys a wearable computing device of the present invention.

The system of the present invention has a strategic partnership with game developers to add outputs to the system to enhance gameplay and make it more interactive.

The game incorporates head movements he makes during gameplay. These movements come from the accelerometer in the headband of the wearable computing device.

He becomes an even better dancer, and improves his ranking in the gaming guilds he's a member of.

Eventually, Roc gains entry to a prestigious dancing school based on how much practise he's had with his devices as a competitive gamer.

The value proposition for this user story may include:

This functionality would allow gamers to have improved gameplay with music- and dance-based games, with more interactive fun and enhanced participation.

Sensors used may include: Accelerometer; gyroscope; microphone.

Applications may include: Gaming, dance education, dance and music therapy, physical therapy, cardio exercise.

Example Application: Caregiver Interaction: L.1 Autistics and Alzheimers can Hear Other's Emotions Encoded as Music (L1)

The following is an illustrative user story for this example application:

Al has an autism spectrum disorder. This disorder makes it difficult to interpret emotions in others based on visual information like affect, and difficult to express emotion in a way that others who are neurotypical can understand easily.

However, Al responds to music and can infer emotion from it. Music is one of his ways of communicating and sharing feelings. It was how he first learned about the various nuances of emotion and affect.

A loved one or care-giver of Al's wears a wearable computing device of the present invention. The system of the present invention detects salient emotion being expressed by its wearer by analyzing and classifying their brain waves into brain state. Brain State responses that are greater than contextual baseline are used to drive musical phrases known to be associated with emotion.

While wearing the wearable computing device, Al can "compose" his emotions by creating complex musical phrases based on his feelings. This is easier for him than communicating verbally or in writing.

The value proposition for this user story may include:

This allows people with an emotion understanding deficit to improve their understanding of another's emotions. It can make them more responsive and improve their relationships with other people. This method can also be used to help people understand their own emotions through music and can have therapeutic value. The same set-up can be used with Alzheimer's or other patients that have difficulty interpreting emotions in others.

Sensors used may include: brainwave sensors

Applications may include: Home care of patients, therapy, training.

Figure 8:
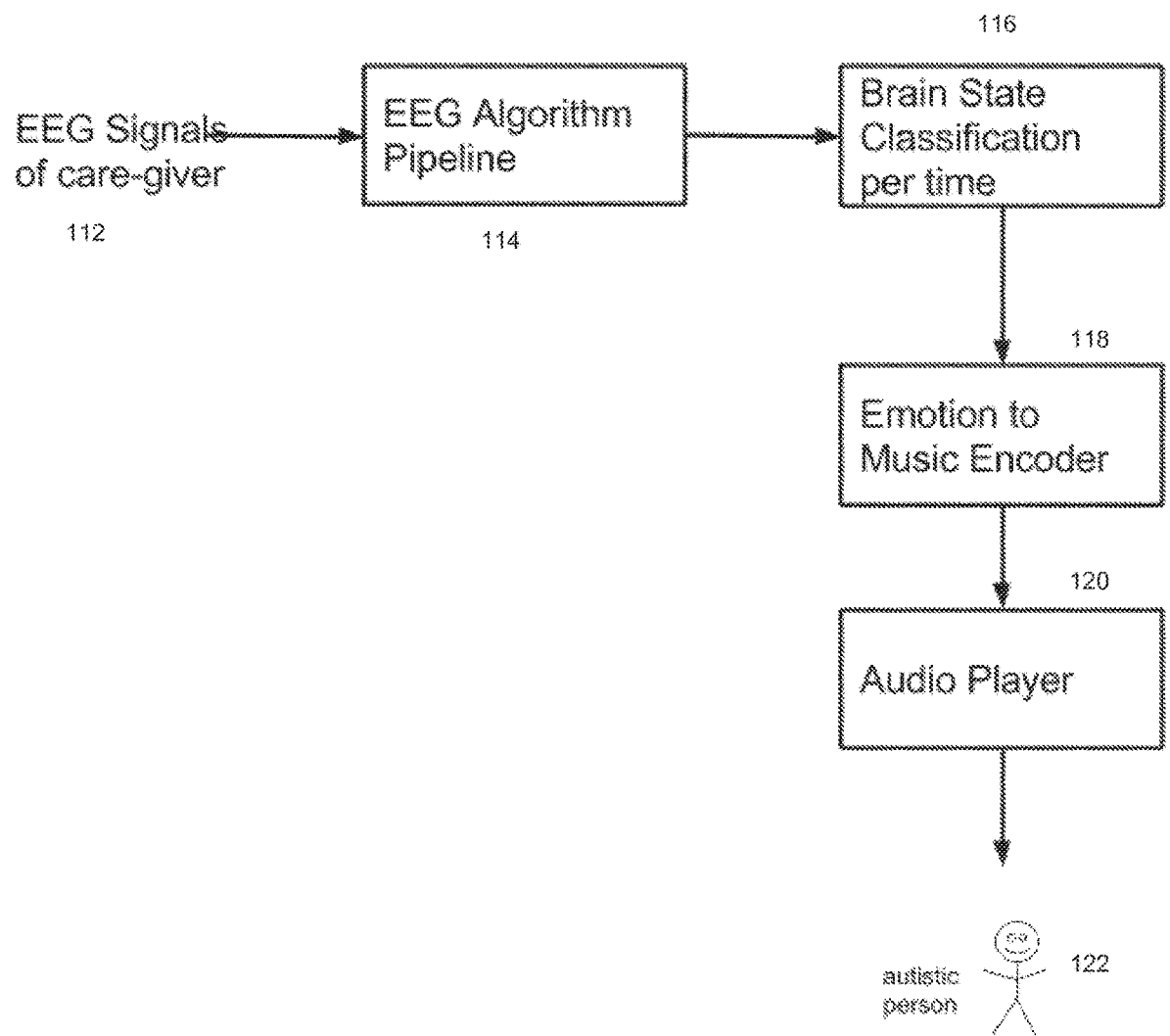
FIG. 8 illustrates an exemplary architecture in accordance with embodiments described herein.

FIG. 8 shows an architecture drawing of the system of the present invention for an implementation of this user story with EEG signals of care-giver 112, EEG algorithm pipeline 114, Brain State Classification per time 116, Emotion to Music Encoder 118, Audio Player 120, and user 122.

Example Application: Stimulation Technologies

The following is an illustrative user story for this example application:

A user is wearing an EEG headband to analyze their brainwave characteristics while the user does a mental and or physical exercise. The exercise may have environmental stimuli such as background sounds, lighting, music etc. or lack of stimuli such as total darkness, or silence. A user's brainwaves and other physiological signals are analyzed and interpreted to provide a characterization of the user. An example is the amplitude of the peak power and frequency emitted by the user in the alpha range (8 to 13 Hz). An external stimulation device such as Transcranial magnetic stimulation The value proposition for this user story may include:

can be used to enhance the user's ability to produce the alpha peak and therefore enhance their ability to enjoy sensory input such as music.

Additional Intelligent Music Features

Another illustrative example User Story is Mindfulness of Music and Sound.

A user is played sound/music during a session. This could be: a. random snippets of sound at random times (birds chirping, someone making dinner, a protest march, classical music, etc); b. continuous sound with predictable changes; c. dynamically adjusting depending on the state of mind of the user: increasing difficulty as the user has more focus and less difficult if the user is distracted; or d. user has the ability to choose their difficulty level, for example.

The EEG monitor tracks their state of distraction during the session.

The user has the ability to turn on feedback of their distracted state. The user gets a score at the end of the session.

A distracted state, for example, may be thinking of the future (predicting what is going to happen) or remembering the past, or attention drawn to physical sensations (rather than the anchor of sound), drowsiness (laxity/dullness) or having any feeling except equanimity, joy, loving-kindness, or compassion.

In an aspect, embodiments described provide a system and method for music recommendation and effects using biological data.

A system and method may characterize music based on digital signal processing of epochs of a song to describe parameters related to human perception. Examples parameters or attributes include brightness, bandwidth, tempo, volume, rhythm, and so on. Data may also describe how these features change over time. These may be called sonic parameters of a song. An epoch is a length of time in how a piece of music is divided. An epoch may be short enough to capture variety, such as for example 200 ms. A user's music preference of songs may be calculated based on their choices of preference when comparing like/dislike across numerous pairs of dissimilar songs.

A human response to music can be characterized by a variety of means; examples among these are behavioural measures such as rhythm entrainment as measured by movement of one or more parts of the body, physiological changes in breathing, heart rate and heart rate variability (HR and HRV), muscle activity (EMG) or galvanic skin response (GSR), and especially changes in brain activity as measured by continuous or epoch-based electroencephalography (EEG), hemispheric asymmetry, and event-related potentiometry (ERP) corresponding to discrete or repeated events in the music or the acoustic environment. The brain responses in particular often correspond to specific listener experiences relating to emotional or arousal/engagement state.

Examples of continuous EEG measurements which reflect perceptual, emotional, or arousal/engagement to music are, but may not be limited to, spectral band power including relative contributions of delta, theta, alpha, beta, and gamma waves. They may also include synchronization or desynchronization (ERS or ERD)

One example of EEG measurement useful in distinguishing both the emotional valence (happy/sad) and the arousal (intensity) of music is alpha power.

When an element of music or the auditory environment changes, for example by increasing or decreasing in amplitude, or changing in frequency or timbre, these changes can be detected as transient changes in the electrical potential of the brain. Some of these changes in measured brain potentials are sensitive to entrainment or musical experience, wherein repeated exposure can enhance the strength of the signal detected by EEG.

Another form of evoked potential, the auditory steady-state response, has amplitude or phase components related to the listener's level of attention to the music or sound. Another potential may be referred to as the auditory mismatch negativity (MMN) reflects an unexpected change in a pattern of rhythmic, repeated sound stimuli, and can be detected in EEG using electrodes near the mastoid process behind the ear. Similarly, the early right anterior negativity (ERAN), which reflects the interaction of a music stimulus and the listener's memory, can be measured with a few electrodes located in the temporal and frontal areas of the scalp.

Embodiments described herein may provide music processing hardware (e.g. DSP) that extracts a set of sonic features from music data. The music data may include multiple songs over one or more time periods. The music data may be defined temporally to map to sensor data captured at different times. For example, a song is divided into N time epochs. A set of sonic features is extracted per epoch where V1 is the vector of sonic features per epoch 1, to VN vector of sonic features for epoch N. In addition, meta data for each song is provided that describes the artist, genre, release date, etc. A set of features can be calculated for all music and this set is known as Music-Everywhere-Everything (MEE).

Embodiments described herein provide music processing hardware that adds features extracted from biological data (from bio-signal sensors) about users (e.g. at playback of music) per epoch of music, temporal characteristics of user's song choices in portable music player devices (e.g. iPods), a user's personality or user attributes, and expert input. The biological data may be used to compute the user's level of engagement, valence and arousal with the music data on an epoch per epoch basis. This may provide a richer way of characterizing a user's response to music and build up models that may help predict more accurately which music selection a user will prefer. Also this process can be used to data-mine across a large population of users their biological reaction to music pieces. The distribution of biological reactions to a specific piece of music may be highly correlated.

Figure 15:
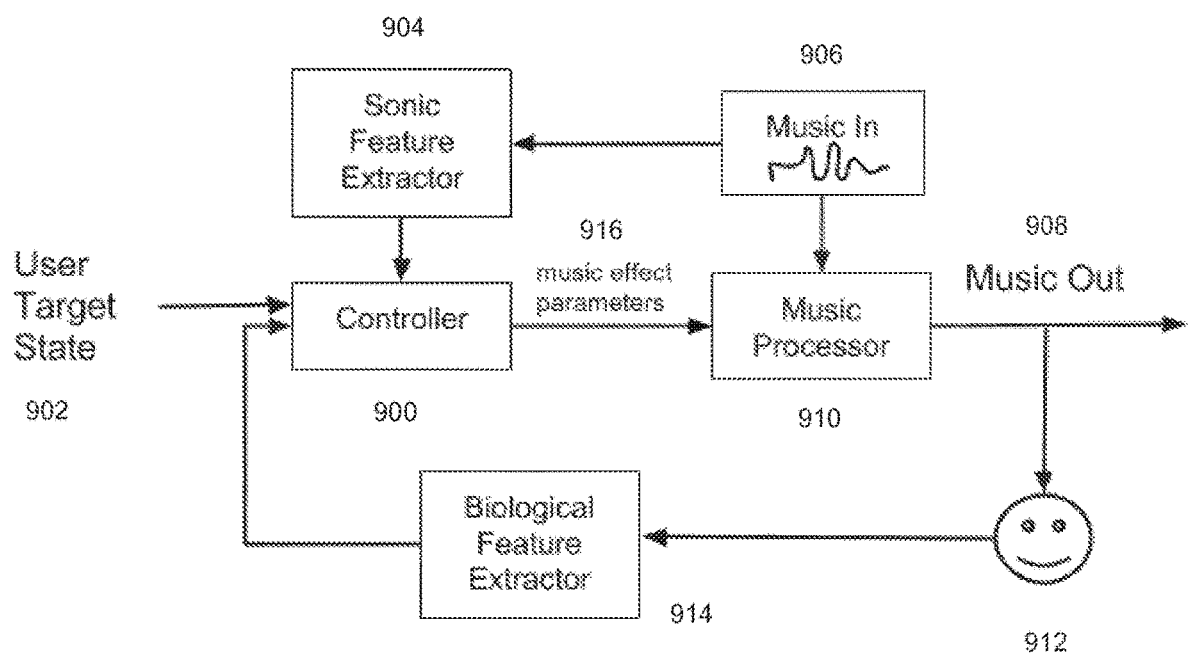
FIG. 15 is a system view of a control system that changes the effects of the music to match a user's desired target state.

Users whose biological reaction differ from the norm may be treated separately and in their own cluster as to what music selections they will prefer. In addition, a system and method are described where effects can be added to existing music to help a user achieve a target state 902 (FIG. 15).

Embodiments described herein provide music processing hardware devices, systems, and methods that add temporal history to the selection of songs selected by the user. The temporal history of a series of songs listened to by a user are described using the following notation.

As an illustrative example, Sa is song A.

Further, Sa(t,i,j) may indicate that a user listened to song a at date and time t starting at ith percentage fraction of the song and ending at the jth fraction. Example Sa(Mar 15-2014-2:01, 0, 1) means that the user started listening to the song Mar 15-2014-2:01 and they started at the beginning "0" and listened to the song to its completion "1" 0

T(Sa(t,i,j), Sb(t,i,j)) may be the transition from listening to song a to song b.

Further, associated with Sa(t,i,j) is a set of features that describe the sonic properties of the song, meta data of the song, and the user's reaction to that song based on measuring their physiological response on an epoch by epoch basis.

As an example, features of Sa(Mar 15-2014-2:01, 0, 1) may be:

V1, V2, . . . VN—set of sonic features per epoch of song.

B1, B2, . . . BN—set of biological features of the user's reaction to a song using the same epochs for the sonic features. The set of biological features can include those extracted from EEG, EMG, ECG, GSR, as an example. In addition, the accelerometer features that describe the motion of the user are also extracted.

M1, M2 . . . Mm—set of meta data for the song. For example, Artist, year released, name of song, genre.

P1, P2, Pp—set of user profile characteristics that can include: birth year, birth city, genre preferences, gender, and so on.

U1, U2, . . . Uq—set of user actions taken during the playing of this instance of the song. Examples are turned the volume up. Adjusted the equalizer such as bass and treble settings. Other features are that this song was specifically selected by the user or this was just the next song in the playlist. Sometimes a user sets their music player to shuffle songs so an action could be that this song was skipped after listening to first 5 seconds. Another set of actions is that this song is part of a user created playlist. People can shuffle songs in the context of artists or genre or release year, and so on.

C1, C2, . . . CN output from Supervised Machine Learning or Unsupervised Machine Learning are set of labels or classes associated with an epoch of music. This is the output of the predictive model. These may be used in supervised machine learning to create the predictive model.

Precise Universal Time-Stamps

Embodiments described herein provide music processing hardware that provide precise universal time-stamps in music data to map to time-stamps biological data and other data sets.

Music requires precise time-stamps. With digital technology, tracks may be clipped. It is important when tagging a piece of music with emotion (via bio-signal data) that it corresponds with the music event data (e.g. note) that evoked that emotion. This may enable a large number (e.g. thousands of user's responses) to be synchronized to the same musical event that evoked the emotion. In this way, machine learning and statistical analysis may be applied to precisely the same moments in music data across a large population users (as expressed via bio-signal data). Music tracks may be standardized as to when a track starts so that time-stamps are universal across all presentations of a specific track of music. A specific note that is characteristic of the song may be tagged with a time-stamp as the start of the song, i.e. START-NOTE.

A user may have a continuous or never ending history of songs that have been listened to. The history of songs may be defined as music data. One example sequence is: . . . Sa(Mar 15-2014-2:01, 0, 1); Sd(Mar 15-2014-2:10, 0.2, 0.9); Sb(Mar 15-2014-2:14, 0, 0.8); . . . .

EEG can be used to infer a user's emotional response to music data using event related synchronization or desynchronization, event related potentials, asymmetry across hemispheres, coherence across a set of electrodes, and power in specific frequency bands. EMG can be used to determine a user's level of muscular tension, their movement in time. ECG can be used to infer the level of a user's arousal. These biological features can be correlated to the sonic features of the music using universal timestamp mapping, for example.

Different sensors may capture and provide different types of bio-signal sensor data. For example, an accelerometer and gyroscope may be used to infer if the user is moving synchronized to the music (e.g. dancing). Accelerometer and Gyroscope can be used to classify rhythm in music and match to user's movement, or detect any rhythm in user's movement, for example. If a user is moving in rhythm to the music then this can be used as an input to classify the level of engagement of a user with the music, and the likelihood of entrainment and engagement with a particular rhythm which may in turn indicate the likelihood of a user's preference for other songs or musical excerpts with similar rhythms.

Category of an Epoch (C1, C2, . . . CN)

An epoch can be labelled with a set of one or more categories that the epoch belongs. Categories may be nested in a hierarchy or an ordered list since a number of states can co-exist in the human body simultaneously. Categories may be expressed as a probability of the class or nominal label. Example categories may be as follows:

Preference of music: like/dislike etc. or valence.

Emotions: Positive or negative states someone is not necessarily directly aware of.

Affect: When one becomes aware of their emotions, or expresses them overtly (such as smiling or frowning).

Mood: A general, overall emotional state based longer-term changes in emotion. Can be inferred from regular reports of affect.

Physiological states: sleep stages (awake, drowsy, deep sleep, REM), arousal.

Cognitive States: mental effort, task engagement, frustration, focus.

Motion and muscular contraction, Tension, Walking, Running, Sitting

All of the features may be stored as data structure in a cloud based storage implementation, as an example. One example is that people are wearing sensors such as brain sensing headbands, and other biological sensors that are connected to a mobile device (e.g. using bluetooth, NFC, wireless). The device plays music and collects the biological sensor data. All of the streams of data flowing through the music player/biological sensor integration device tag the streams with time-stamps so that all of the data that occurred simultaneously are tagged with the same or a corresponding time stamp. The device can upload the data (music, biological sensor data, user actions, music meta data, etc.) which can be uploaded to a Cloud for storage and processing. Please refer to Applicant's U.S. application Ser. No. 14/115,781 entitled Systems and Methods for Collecting, Analyzing and Sharing Bio-Signal Data and Non-Bio-Signal Data, the entirety of which is incorporated by reference herein, as reference for how cloud storage may be used to process the data, create predictive models and create analysis algorithms that are used to interact with functionality described herein.

One example of determining a predictive model is the Hierarchical Temporal Memory (HTM). HTM can infer the next set of features that will have high likelihood or probability to create an emotional response in a user. A song is recommended to the user. The user can accept, or modify (i.e. reject, or choose another song) the system's music recommendation. This may be referred to as MANUAL OVERRIDE or feedback. The user's choice can be used as additional information about the song (e.g. metadata) and the user's preference of that song.

The predictive models of embodiments described herein may have a learning mode and an operational mode. The learning mode may be where the model is being updated as new information arrives based on user choices and biological reactions to songs. Sometimes the choice of next song that is offered may be random and based on the biological reaction of the user can be used to determine how anomalous the system's recommendation. Random choices and/or songs that are not part of the usual space of choices may be useful to expand the accuracy of the model by probing new genres that may be of interest to the user.

Operation mode occurs when the model offers a recommendation of a song to the user.

Smart Playlist Controller

In an aspect, there is provided a music processor that provides a smart playlist controller. The smart playlist controller may generate queries or questions to receive additional information about a user.

Example questions for User to help select music may include:
1. How do you feel right now?
2. How do you currently feel? How is the current music making you feel? or
3. What is your goal emotion? or How do you want to feel? or What kind of music are you looking for? If you are sad and want to hear sad music then user is looking for empathy. If the user is sad and want to happy then they want to improve their mood.
4. Based on answers to questions 1-3, select appropriate music. (PROCESS, OUTPUT)

The smart playlist controller may automate selection of music for the user that will help them meet their goal emotion according to some embodiments. The may help automate questions 1 and 2. User input may be required for question 3. Step 4 may generate output of embodiments described herein.

The user can select a target state that they want to achieve, which, as an example, may be on two axis. One axis may be a level of energy and the other access may be a level of engagement or attention they want to invest in the music. Sometimes people may want unobtrusive background music and other times they want to engage 100% of their attention in the song. In addition to the state that the user wishes to achieve, their current biological state as inferred through analysis of their biological sensor data may be displayed on the same two axis.

Figure 10:
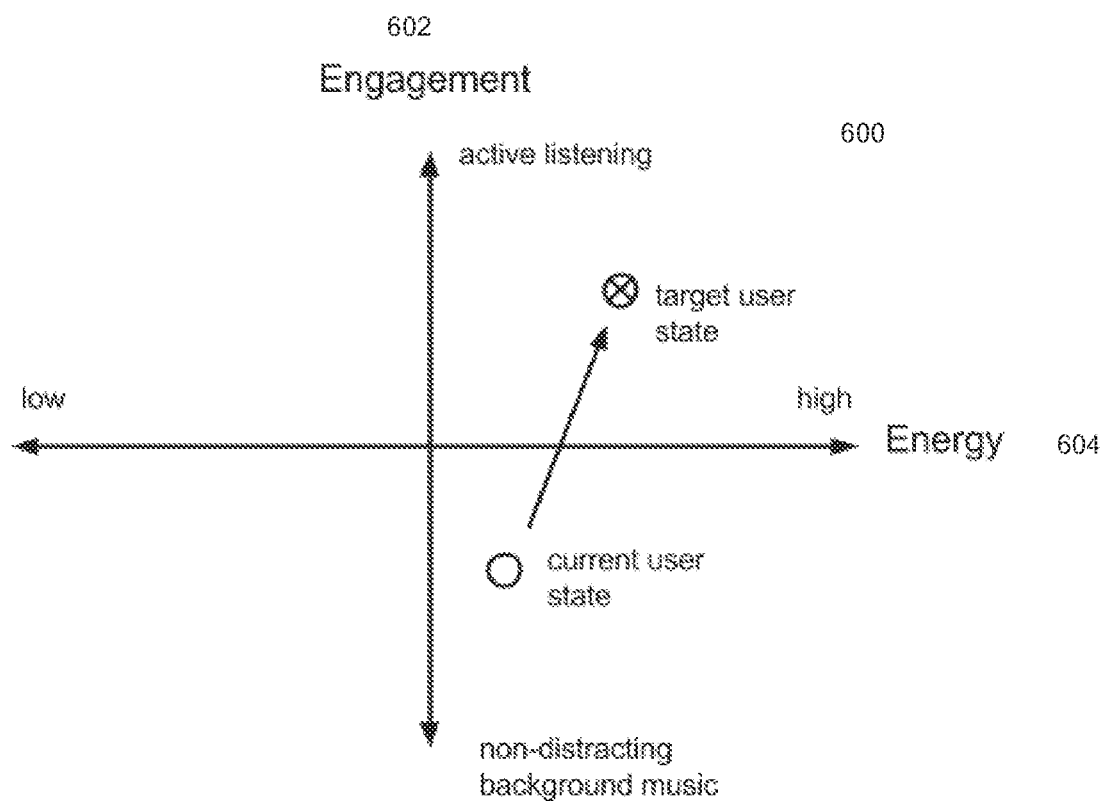
FIG. 10 shows an example of a user interface for describing the current user state and target state according to some embodiments.

FIG. 10 shows an example of a user interface 600 for describing the current user state and target state, which may display an Energy 604—Engagement 602 matrix which may be an interactive space for user input.

In another example of target state, the user may choose along Valence and Arousal (VA) by a selection on an input device (e.g. touchscreen display). In these dimensions, Valence may be on one axis with "approach motivation" (feelings of positivity) on one end, and "avoidance motivation" (feelings of negativity) on the other. The other opposing axis may be Arousal, with high intensity of feeling on one side and low intensity on the other. Commonly-felt emotions traditionally fall within the quadrants formed by that VA matrix. Again the user's current state (i.e. the answer to question 2. above) may be displayed on the VA matrix and they press on the VA matrix where they want the music to take them. See FIG. 11 for an example of this user interface 610 with a valence 614 arousal 612 interactive space for user input.

As an illustrative example, the user can select that they want more energy for interacting with a section of the matrix shown in an interactive display, for example. The difference between the user's target state and their current state may be represented as a vector. This vector can be used to select or recommend songs that may help the user achieve their target state. The user for instance can express the desire to be happier as a target state. The difference between their current biological state and their target state (i.e. as represented by a data structure vector) can be used to select the attributes of the music to offer. If there is a large difference in happiness from a user's current state and target state then songs with greater scores for happiness may be offered to the user.

Another way for the user to express their desired target state may be by selecting a word from a list of words offered to the user in a display interface. The list may include selections such as happier, energetic, relaxed, peaceful to represent a desired target state. These can be isolated into a section of the Valence-Arousal (VA) quadrant. As described, the user's current emotional state may be located in the VA plane. A vector can be found from the user's current state to their target to drive the type of music that they wish to hear.

How to Determine the Emotional Tone of a Piece of Music

Figure 12:
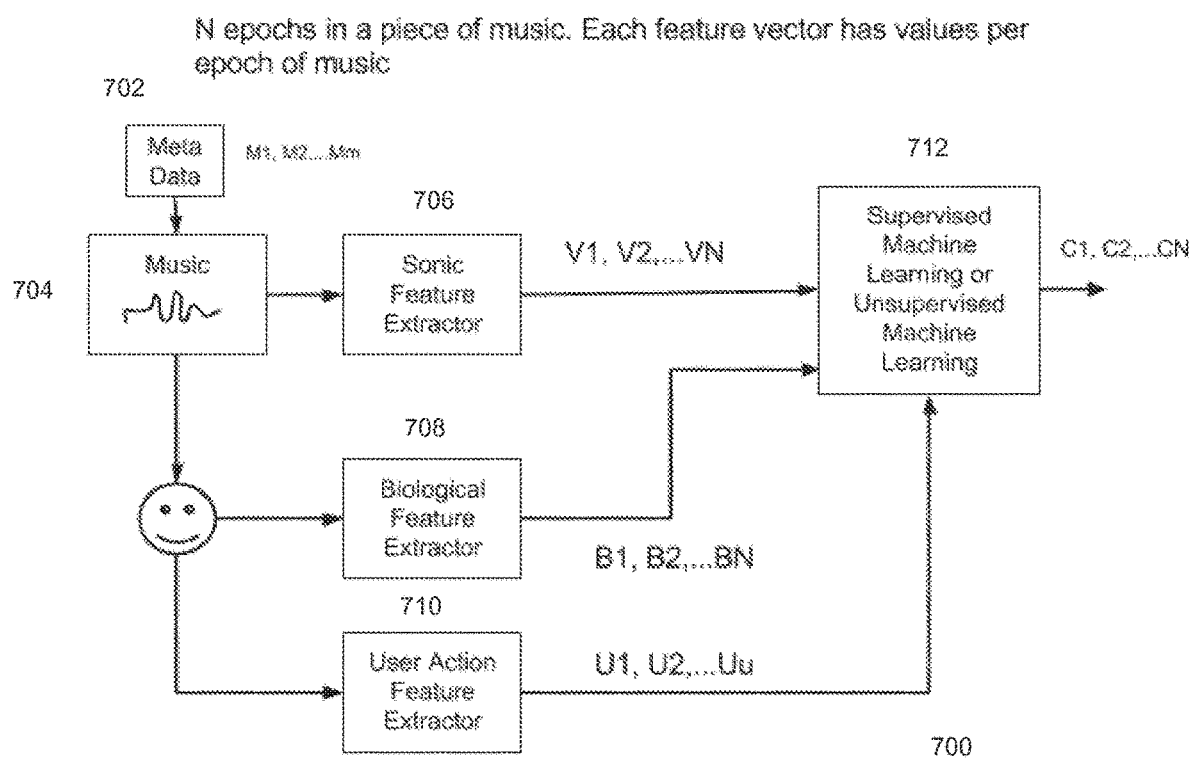
FIG. 12 shows a system view of extracting sonic, biological and user actions and using machine learning to determine a predictive model of the music data and the user's reaction to it.

FIG. 12 shows an example architecture to implement a predictive model engine 700 according to example embodiments. The model engine may predict human reaction of music 704.

In general, there may be strong agreement across many people as to the emotional tone of a piece of music. Most people may agree that a piece is happy, sad, romantic, energising, and so on. The association of a song to its emotional tone can be learned across many people (and bio-signal data associated with the many people) inferred from their biological features or it can be part of the meta data of the song, for example. Italian musical terms of classical music is an example of meta data describing the emotional tone of a piece of music such as con brio (with vigour), dolce (sweet), dolente (sad), dolore (grief) etc. Using biological features along with their corresponding sonic features of a piece, embodiments described herein may be configured for machine learning 712 (supervised machine learning or unsupervised machine learning) of the biological signatures per epoch associated with the sonic features of the epoch of music. Music is an emotional language and composers use its vocabulary to create emotional tone for their piece. A sad song may have a lot of minor and diminished chords to it, for example. A happy song may be set in major keys. Angry music may have a driving beat and minor keys. A key is a pattern of notes that makes up a scale. The keys of music may be defined in music data. Different keys have different patterns of notes separated by different intervals. It is the different intervals between notes that distinguish major keys from minor keys. In addition tempo (rate of speed of music) can affect the emotional tone of music, for instance slow tempo make music seem sad. Passages of music with known emotional tone can be used as labelled training data for supervised machine learning. The emotional tone of music of part of the meta-data 702 of the music piece may be represented as M1, M2, . . . Mm. Music processing hardware may process music data 704 to extract meta-data 702.

Detection of Approach and Avoidance may be implemented by some embodiments, for example. Alpha asymmetry across brain hemispheres may be a measure of approach and avoidance. Heart rate goes up and down with arousal. Heart rate goes up both with a response of excitement and also an aversive response. Changes in body tension can also be a sign of aversion but also excitement with anticipation of a release.

Two methods are described herein of creating a model to predict the emotional impact of music on a user as illustrative examples. The first example method is a two-stage method. First, the labelled epochs of music may be used to train the system with the sonic features of those passages. Example types of supervised machine learning include support vector machines, deep learning neural networks, decision trees, logistic regression, linear discriminant analysis and others. In addition, temporal information can also be encoded using Hidden Markov Models. Using a supervised learning method a model can be trained by system based on the known examples of labelled epochs of music. For unknown pieces of music the model generated and implemented by the system or music processing hardware can be used to predict the emotional tone of a piece of music based its sonic parameters represented as V1, V2, . . . VN (from Sonic Feature Extractor 706). The model for predicting the emotional tone of music based on its sonic parameters can be used to classify all music of interest. In this way a small set of human labelled music can be used to classify, using a configured machine, a large catalog of music data. The second stage is to learn the biological or bio-signals evoked when a user listens to a piece of music and their extracted biological features B1, B2, ... BN (from Biological Feature Extractor 708). The model is built the same that results in a predictive model of classifying a user's biological signals into an emotional state.

The second example method uses unsupervised machine learning methods such as HTM or deep learning where training the combined features of both biological and sonic parameters simultaneously. One example is the Hierarchical Temporal Memory (HTM). The deep learning method works by using several layers of stacked two-stage (hidden, visible) restricted Boltzmann machine. Deep learning can discover the model of the data using unsupervised methods. Deep learning may be used for optical character recognition and speech recognition, for example. In addition adding Hidden Markov Models to the output of deep learning can improve the accuracy prediction by bringing in temporal characteristics of the music. All of the features of both the sonic parameters of the music and biological parameters can be fed to the model. If there is a sufficient number of training samples, the raw itself (notes, voltage values of samples biological data, and so on) can be used to train the deep learning networks. Once a deep learning process implemented by the system or music processing hardware has learned the data either through its features or its raw data, the data can be provided as labelled examples to turn the deep learning network into a predictive model. Then the network and the weights can be optimized by the system or music processing hardware for further refinement.

Another example of improving the accuracy of the categorization of a piece of music is to use Hidden Markov Models. As explained above happy music may be written in a major key while sad music may be written in a minor key. Numerous examples of music with major keys and minor keys can be used to train two different Markov Models. The Markov model may be expressed as a set of states and their transition probabilities. A state in this case may be a set of features (e.g. representative of a note and the tempo of change from a preceding note). All examples of music in a key can build a model that captures the probability of sequence of notes and tempo from a starting note. So one model is built for major key Model1 and another model is built for minor key Model2, as an illustrative example. The sequence of a set of notes can be described from their vector of features V1, V2, ... Vi. An unknown piece of music has two aspects which may be calculated:

$p(V1,V2, \ldots Vi|\text{Model1})*p(\text{Model1})$–conditional probability of feature vector given model 1 times probability model 1

$p(V1,V2, \ldots Vi|\text{Model2})*p(\text{Model2})$–conditional probability of feature vector given model 2 times probability model 2

An unknown piece of music can be classified as belonging to Model 1 (major key) or Model 2 (minor key) by choosing which of the above equations has the higher value. This piece of information can be used to revise the sonic parameters of a piece of music by including this label (sad or happy) into each epoch that was used to determine the key.

The process described herein can also be used to improve the classification accuracy of the biological state of a person. In this case $p(B1,B2, \ldots Bi|\text{Model1})*p(\text{Model1})$–conditional probability of feature vector given model 1 times probability model 1.

$p(B1,B2, \ldots Bi|\text{Model2})*p(\text{Model2})$–conditional probability of feature vector given model 2 times probability model 2.

Like and dislike of music pieces by an individual is a separate dimension than the emotional tone of music. The emotional tone of music is an important determinant of whether a user will like a piece of music but other factors are present as well. The like and dislike of music can be partially determined from the user's action when selecting music, i.e. features U1, U2, ... Uu (from User Action Feature Extractor 710). For instance increasing a piece's volume, whether a song is skipped, the frequency of playing a song are examples of features that are associated with like and dislike of music.

These models can be trained across a population of users whose biological signals have been recorded while listening to music. These general models can be fine-tuned to specific users. One way is to use manual over-ride or user feedback which is described herein. If sufficient data exists for a user then a customized model can be trained for them using the methods described herein. Another method is to match this user to others using meta data about the person. For instance age, genre of music, favourite artists, etc. This can help localize within the universe of users that have similarity to this user and using that data to develop a model for that sub-group of users.

Manual Override or Feedback

The machine learning methods described herein can be fine-tuned for each user. The biological signals of a user while listening to music may be used to train a model for that user. The user may choose to ignore the choices offered by the system. This manual override is also input to the system to help it learn the user's preferences. The user may revise their vector to emphasize that the choices suggested by the system are not happy enough. In addition, the user's preferences can be used to develop a model of like/dislike of music and that person's preferences.

Figure 14:
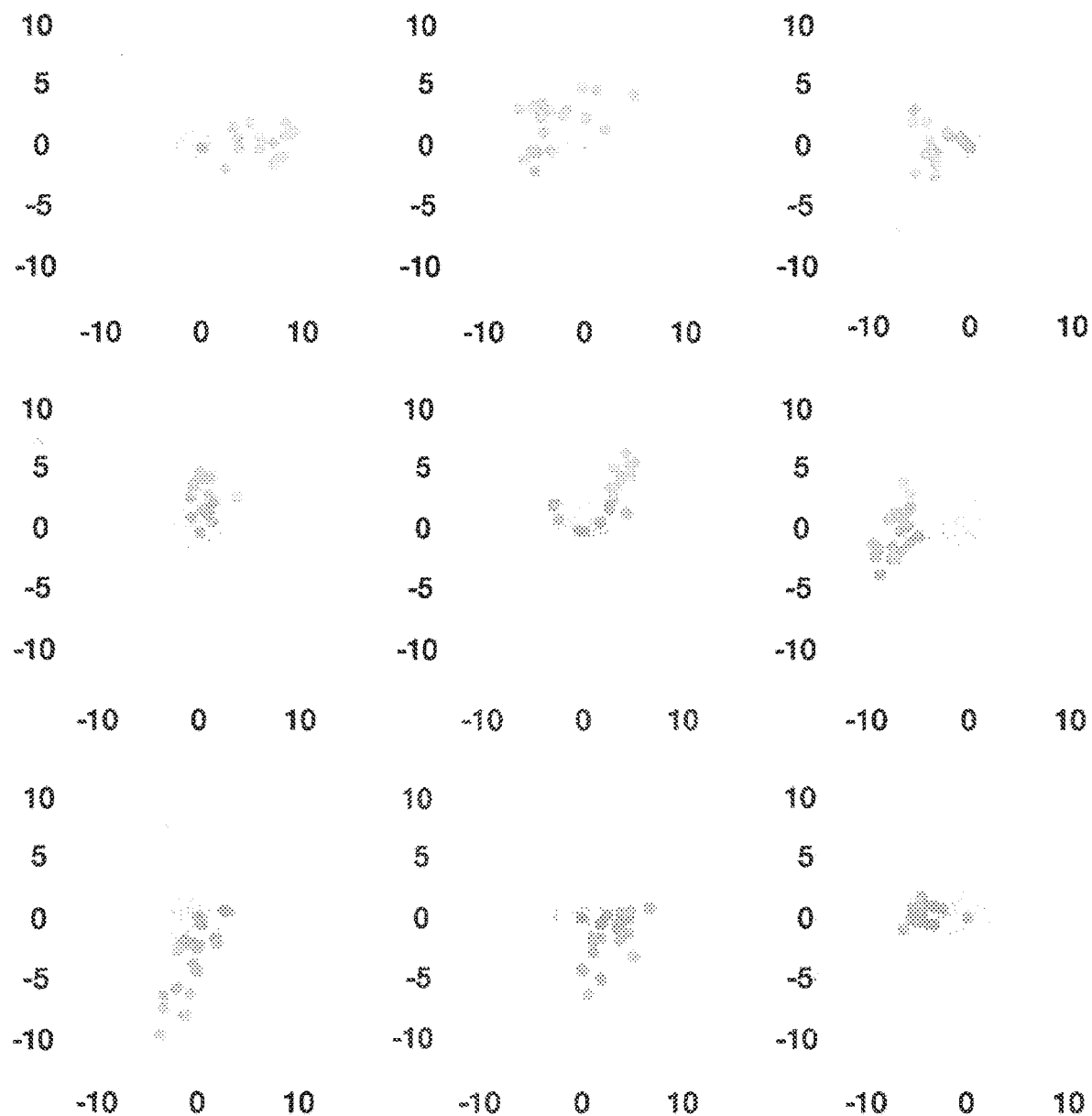
FIG. 14 shows a graph with an example of 9 different users.

EEG and the other biological signals allow us to estimate the user's current state of engagement with the music, valence and arousal. FIG. 14 is an example of 9 different users, of several sessions where users undergo a memory recall exercise of categories. These are unique signatures of each individual that tend to cluster tightly compared to a large population of other users. This information can be combined with the time of day to capture the patterns of change that happen with varying circadian rhythms and sleep pressure. The location of an individual's cluster can be compared to the whole. Models can be customized to an individual and as well as adapt over time by comparing the statistics of features related to the an individual's cluster to the population as a whole. Also models can be specific for sub-groups based on age, gender, handedness. These covariates are known to be associated with certain biomarkers of EEG information.

Another example is clustering of sessions of individuals. In the PCA space, sessions of the same users tend to cluster together. Each plot represents the PCA cluster of an individual. All the sessions of a 9 users were chosen at random from our cloud data. The plot reveals that a user's relative EEG power tends to cluster in a local space. This can be used as a biometric marker of that user. The lighter points each represents a single session. The larger dots are increased the size correspond to the sessions of a unique user.

This information adds another dimension to people that are brought together over the love a song. People whose clusters overlap may exhibit similar personalities or tastes.

Figure 13:
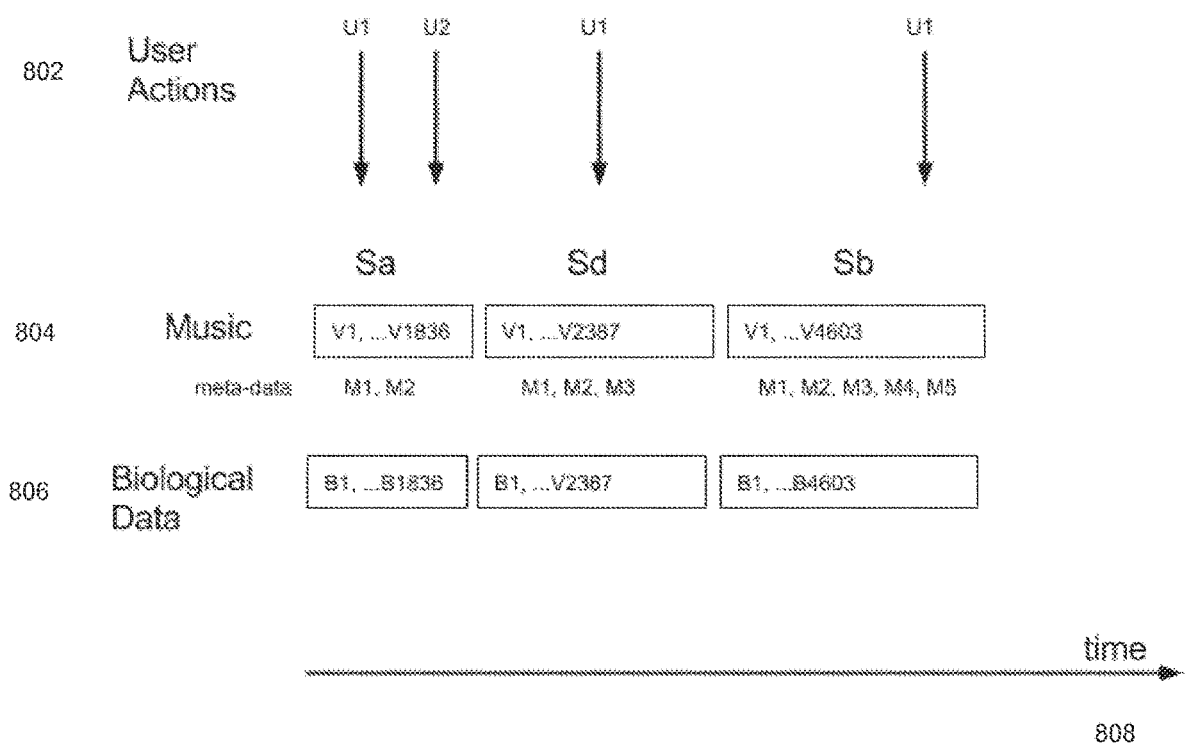
FIG. 13 shows a time representation of the features shown in FIG. 12.

FIG. 13 illustrates a temporal modelling of sequence of music choices from user actions 802, and shows features extracted from a sequence of songs provided as input as music data 804. An Example of notation of a sequence of songs may be . . . Sa(Mar 15-2014-2:01, 0, 1); Sd(Mar 15-2014-2:10, 0.2, 0.9); Sb(Mar 15-2014-2:14, 0, 0.8); . . . .

The system adds temporal information of the sequence of songs (shown over time 808). The new set of data may be referred to as Music-Everywhere-Everything-Temporal (MEET).

These stream of songs Sa, Sd, Sb, . . . and their associated features including the user's biological response 806 may fed into the system or music processing hardware as input and may be used for unsupervised learning of temporal models. One example is the Hierarchical Temporal Memory (HTM). HTM learns the structure of the data based on the temporal order of the features it is fed. HTM can be used to determine the novelty of an event of data that it is fed. For a given event k and based on the sequence of events prior event(k−1),event(k−2) etc., HTM can determine the likelihood of an event k. This model may be continuously updated by the system based on the user's behaviour as input by bio-signal data. HTM learns to understand a long chain of temporal events. The embodiments may not considers music pieces as sole or isolated examples in the training data and may consider the temporal relationships revealed by listening to music one selection after another.

Another example of temporal modelling is using Hidden Markov Models (HMM). According to some embodiments, an HMM can describe a network of transitions from one song to another showing the probability of transition from one song to another. For example, a user is listening to the Beatles song "Let It Be" in the album of the same name. By looking across user choices of next song it could be revealed that the next song to be selected is "Maggie Mae" with a high probability. This is because "Maggie Mae" is the next track in the album "Let It Be". However, with digital music, a user is not constrained to hear tracks in this order and the order of songs is based on some goal or mood that the user wants to achieve. The order of songs selected can be useful in choosing songs that are tied together. The set of songs after the current song listened that have high probabilities of being selected form a cluster of songs. These clusters have a great deal of similarity and can also be labelled with meta data such as artist and or genre. The clusters can also be considered "genres" in themselves. These clusters based on high probability of being played after or before a song can also be called "genres" and can be added to the meta data of the song that can improve the machine learning models that are created.

FIG. 14 shows example graphs 900 of clustering of sessions of individuals.

In the PCA space, sessions of the same users tend to cluster together. Each plot represents the PCA cluster of an individual. All the sessions of a 9 users were chosen at random from our Cloud data. The plot reveals that a user's relative EEG power tends to cluster in a local space. This can be used as a biometric marker of that user. The smaller light grey points each represents a single session. The darker larger dots are increased in size to correspond to the sessions of a unique user.

FIG. 14 shows the architecture of a Music Effect Controller to influence user state.

As an illustrative example, a Disc Jockey (DJ) is a person that mixes and adds effects to recorded music to a live audience. A human DJ can interpret an audience's reaction to help them improve the level of engagement and satisfaction that an audience receives from their performance. A relationship and communication form between the DJ and the audience. The DJ is doing a live artistic performance and they have many tools on hand that can affect the underlying recorded music that they are working with.

Figure 11:
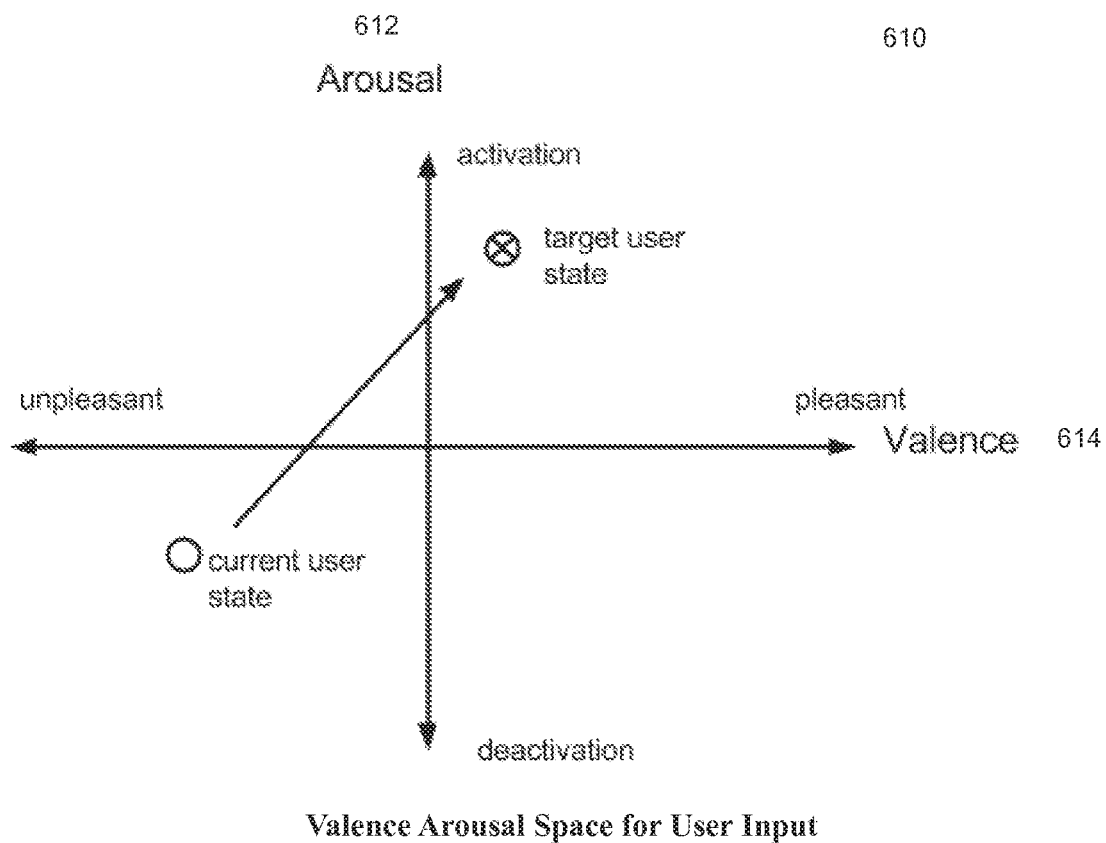
FIG. 11 shows an example of a user interface with a valence arousal interactive space for user input according to some embodiments.

FIG. 14 describes a system where the user inputs a target state they want to achieve and a control system that changes the effects of recorded or live music. FIGS. 10 and 11 are example user interfaces in how a user can set their Target User State. Biological sensors measure the user's response to the music and features are extracted from these signals as shown in FIG. 12 (Biological Feature Extractor). Also the sonic parameters are extracted from the music as shown in FIG. 12 (Sonic Feature Extractor). The controller changes the effects its applies to the music data to be output by setting the parameters of the Music Processor. The controller uses feedback from the Biological Feature Extractor and the features of the music output from the Sonic Feature Extractor to change the parameters (music effect parameters) of the Music Processor to adapt to helping the user reach their desired Target State.

The following is a list of Music Effects that the Music Processor can apply:
change of tempo
filtering—changing the amplification level of different frequency bands in the music
changes in left/right balance
reverberation
spatialization
room models
pitch shifting
chirp effects
vocoder (human voice as notes)
auto-tune
auto detune
humanize electronic music
the order of samples of music may be changed (i.e. the chorus and verses may be ordered in different ways to change the order the music is played but the piece is still recognizable.)
profile of tension and release over the course of a piece of music In the method and system described in FIG. 15, the function of the DJ (i.e. Controller 900) may be automated by system by applying a process that automates the DJ's interpretation of the user's 912 reaction. The Controller 900 changes an effect of the music output 908 such as increasing the volume using Music Processor 910. The user's reaction to the change is based on the prediction models of signals from their biological sensors. If a user has a positive reaction the change is kept. If the user has a negative reaction that effect is not added to the music. The rate and number of changes are parameters of the algorithm that can be adjusted based on the preferences of the user.

One method that the controller can use to estimate the Music Effect Parameters 916 is by finding the maximum in the following condition probability:

P(ME|V, B, T) is the conditional probability of the music effects given the sonic features of the music input 906 extracted by Sonic Feature Extractor 904, the user's initial biological state from Biological Feature Extractor 914 and the user's target state 902.
where
ME is Music Effects Parameters
V is the vector V1, V2, . . . VN—set of sonic features per epoch of song
B is the vector B1, B2, . . . BN—set of biological features of the user's current state prior to applying changes in effects
T is the target user state that the user wants to achieve. See FIGS. 10 and 11 for example of how user can set their target state.

P(ME|V, B, T) can be estimated using machine learning techniques such as probabilistic neural networks, logistic regression, Fischer discriminant analysis and other techniques. The range of values of Music Effect parameters can be supplied by human music experts. Training examples can be obtained across hundreds or thousands of users. The model can be general to a population, to a sub-group (i.e. genre) or to an individual.

The Controller uses the features from the Biological Feature Extractor to determine the current User State. In one example the User State can be described by four parameters: a) Valence (positive or negative emotion), b) Arousal, c) level of attention, and d) level of synchronization. Estimating valence and arousal are described in prior art. Level of attention and Level of synchronization is described in more detail herein. See also, for example, Applicant's U.S. application Ser. No. 14/368,333 entitled ADAPTIVE BRAIN TRAINING COMPUTER SYSTEM AND METHOD for a description of how a busy-mind score is calculated, the entirety of which is incorporated by reference herein. Further control details may be found in Applicant's PCT Patent Application No. PCT/CA2013/000785, filed Sep. 16, 2013, the entirety of which is incorporated by reference herein. Further examples of modifying the presentment of digital content may be found at Applicant's PCT Patent Application No. PCT/CA2013/001009, filed Dec. 4, 2013 the entirety of which is incorporated by reference herein.

Music has a beat that can be considered a very strong stimulus to the user. Level of Synchronization can be described by four reactions user has to the beat in the music: one they may be anticipating the beat, be in synchrony with the beat, lagging or not following the beat. In neuroscience Event Related Potential (ERP) are signals seen in a user's brain signals in response to a stimulus. Typical delay for a human brain to process and create a response is 300 ms measured from the time of the stimulus and when the ERP is measured from the user's scalp. i.e. P300 ERP. A user is synchronized with the music when over the course of a minimum number of beats, the ERP associated with the stimulus is less than the typical delay in that response. For instance, the typical delay may be 300 ms but the user is creating ERPs within a range of plus or minus 100 ms relative the onset of each beat indicates the user is in sync with the beat. User is anticipating the beat when their ERP is precedes the stimulus by a minimum say 500 ms in this example. The user is lagging if the ERP is after the stimulus by a large amount say greater than 700 ms on average. The user is not following the beat if the distribution of the ERPs relative to the stimulus (i.e. beat) is random and has whose variance of the difference of the ERP to the stimulus is greater than a threshold and has a two tailed distribution (i.e. the ERP both lags and precedes the stimulus over a range of sequential beats). The Level of Synchronization is strongly related to the user's enjoyment and engagement with the music. If the user is in synch or anticipating the beat then the user is engaged in the music. If the user's synchronization is lagging or not following the beat then they are not enjoying the music or it is too fast for them to follow and it sounds like noise to them.

Another method of detecting rhythm entrainment and engagement is to use a combination of frontal alpha for engagement and emotional valence plus accelerometer data to detect entrained movement (even small movements). People seem to "prefer" a beat that they've already entrained to. We could, simultaneously analyze a musical rhythm, an EEG response, and EMG or accelerometer data to determine a) whether they're entraining to a beat through movement (toe-tapping or head-bobbing, for example) and b) whether their entrainment predicts the tempo and rhythm of the next song/excerpt to play that will generate a positive valence or sustained emotional state. This method can be used to help select the next song that would maintain the same beat or rhythm.

Probing a User to Improve Estimate of their Current Brain State

The system described in FIG. 15 can also be used to estimate the user's current state by using salient parts of a music piece or insert an audio stimulus not part of the original piece of music. Using the ERP paradigm described above, salient audio features or foreign auditory probes can improve the accuracy of estimating the user's current brain state because of the novelty of the audio will tend to increase the size of the user's ERP. For instance, a user's level of engagement can be estimated using a stimulus response paradigm where the stimulus is unexpected.

Meditation Example

The system architecture may implement the following work flow. Step 1: Set up a user's posture using audio feedback. Guide a person into postural alignment using sound.

A user's posture may be set up using accelerometer and sound to give them feedback. A user may be instructed to sit in an upright posture. Once a user's posture starts to stabilize a tone would start "filling-up" and once they hit a crescendo because they have been in that position for a while. Then the user may be asked to move and shift another part of their body. This may cause/destabilize the accelerometer threshold to reset and the crescendo may change alerting the user that their posture has changed. This process teaches the user how the posture correction system works. This creates a 3 dimensional feeling, they feel held, and when one is aided to adjust their body in a unique way they feel that the system is responsive. The users not only feel that the system is reactive but they are being "held" in that posture. The user's perception of the system was acquired using a phenomenological method of inquiry. The approach was built bottom-up using the legs, moving side-to-side, lifting the chest up, dropping the shoulders down, moving the head one way to the next, (left-right, tilt up-down). Proper posture gives more energy to the nervous system, if the body is alert then the mind will be more alert as well. Users have given the following kinds of feedback: "Wow, I never realized how important my body is for an alert mind." The posture setting has a different paradigm than the sound paradigm given for EEG biofeedback (neuro-feedback) described herein.

Future enhancements of the posture algorithm can be used to show the user their posture across the session. This may reveal patterns of behaviour that can help the user understand and improve their posture performance.

Step 2: Instantaneous feedback of a person's brain state. There are several time scales of feedback provided to the user. The first and shortest time scale is moment to moment feedback which is instantaneous feedback. A synthesized tone is generated based on the analysis and interpretation of EEG that changes rapidly from one moment to the next. Example of brain state. This feedback is driven by a BUSY-MIND score which varies between 0 and 1. With 0 being a calm mind state and 1 being the busiest of mind states. See for example Applicant's U.S. application Ser. No. 14/368,333 entitled ADAPTIVE BRAIN TRAINING COMPUTER SYSTEM AND METHOD for a description of how a busy-mind score is calculated, the entirety of which is incorporated by reference herein.

Step 3. Maintain a target state. The next level is a trait feedback when one has maintained a certain state for a minimum period of time or a cumulative feedback. Once the person's busy mind score stays below a threshold (lower the score, the calmer the mind) a tone starts building up rising to a crescendo and then if one maintains the crescendo then it "unravels" into an interesting musical story. Once a person goes above the threshold then the crescendo stops building and is reset to the beginning. From a human interaction perspective this experience there are two points. The sound feedback is layered. Maintaining a target state is less judgmental and more welcoming than instantaneous biofeedback method. It opens up our app to allow it to be possibly used for other exercises such as body scan that require longer periods of feedback. The system is more generous with the feedback that it provides the user. This method is for people who have experience with the current instantaneous method of feedback. People with experience will understand the longer term state that they are being given feedback towards. It may be suitable for people without neuro-feedback experience but a way of showing them how the system responds to their mental state needs to be determined. This type of feedback encourages sustained, diligent practice.

Future improvements of this technology may include providing different sound paradigms for each zone of the BUSY-MIND score. The first threshold is set at 0.7 and this triggers the first sound paradigm. The next threshold of the BUSY-MIND score is set at 0.3. Sustaining the score below 0.3 triggers the next sound paradigm.

DJ System for Meditation Teacher Example

The meditation teacher is able to hear the brain state of each user in a live guided meditation class. A class comprises of up to half a dozen users sitting with headphones and brain sensing headbands. Each user in the audience is having their brain-state being fed back to them. In addition, the feedback of each user is fed to a mixer board that the instructor is listening. The instructor can toggle between each user to hear the brain state of each user. The instructor can also see the brain-state of each user in the audience. The instructor can see each user, the visual brain-state score and hear how the sound is modulated for that user. For instance, a user may be falling asleep and the instructor adjusts their control panel so that user is jarred awake using a sound designed to wake them. In another example of instructor-audience interaction, the instructor would notice that a user is holding a good meditative state. The instructor may decide to further challenge that user by increasing the difficulty threshold of the feedback for the second layer of sound feedback to maintain a target state. In a third example, a user may be having difficulty maintaining a meditative state, in which case the thresholds may be relaxed by the instructor to help user get through the practice.

The thresholds of the feedback may be changing and being manipulated by the instructor. The instructor may be telling the users that he/she will be controlling certain aspects of what the user is going to hear. The users are told that if the instructor sees that a user has a stable breathing pattern then the instructor will change the type of feedback given to the user. The instructor can also choose to bring the audience to a shared experience through musical language. The audience can be cued to create a certain brain state. All of the audience can be brought into a meditative state. The audience can also be agitated using higher frequencies or put into a state of relaxation using lower frequency tones. The audio feedback given to the users need not be biofeedback but can be created by the instructor. The instructor may choose for instance to play a sound track that is similar to the collective mood that the users are in. The instructor develops intuition as to where the audience is at and what they need. This system may also help new facilitators learn how to interpret an audience because they are given additional information about the physiological state of each member of the audience. Other measurements can include group measures of the audience. Scores that the audience together contributes to. Another aspect of this invention is that the instructor can bring the audience into electrophysiological synchrony of their heart beats, breathing rate, and EEG patterns. Physiological synchrony can be enhanced using EEG. There could be a hierarchy that starts with synchronized breathing, then synchronized heart rate, muscle tension, and synchronized EEG state.

This platform can be used to get labelled data about each user in the audience. The instructor can interpret the state of the user based on the user's posture, facial expression, breathing rate, and EEG scores. The experienced instructor can label the data relevant to the meditation experience as user 1 is in state 2, user 2 is in state 4, etc. This can be used as a way to codify the instructor and automate the process of instruction that can be transformed into an application using machine learning techniques.

Networked Meditation Example

A user is doing a meditation session guided by scores driven from analysis of EEG picked up through brain-sensing headband. Through special tones a user is alerted to another user who is meditating in another location, possibly other side of the world. Each user can hear significant events and the state of another person's brain state while each person meditates. This provides a felt sense of presence for each participant sharing their meditative state and hearing the state of others' meditation session. Initially the appearance of another meditator could be signalled by a unique piece of music, i.e. musical appearance. Other states of that meditator can be represented using similar musical theme as their musical appearance. The state of the other meditator can also be music modulated by their state of meditation. After the session is over, the application can alert the user that another person was meditating at the same time and the link to the other person's profile is shown. The other meditator could be somebody on your friend list.

Emotion Scoring Engine Example

For recommendations, the engine processor may use an emotion scoring example. This may be referred to as an Emotion Scoring Engine.

Emotion Scoring Engine may be configured to detect and score the following examples.

Example emotions: Unconscious positive or negative reactions.

Affect: When one becomes conscious of their emotions. In other words feelings.

Mood: A general state based on the average of emotions felt throughout the day.

There may be universal time stamping of music tracks. Music tracks are standardized as to when a track starts so that time-stamps are universal across all presentations of a specific track of music.

With digital technology, tracks may be clipped. It is important when tagging a track with emotion that it corresponds with the music event (e.g. note) that evoked that emotion.

The Emotion Scoring Engine may have EEG Scoring. This may be labelled EEG data as to the type of music a person was listening to is collected and stored in Cloud data. Machine learning is used to develop a classifier of the EEG. EEG can also be clustered based on individual and the type of music that a person was listening to.

The Emotion Scoring Engine may connect to sensors such as Accelerometer and Gyroscope.

This may classify rhythm in music and match to user's movement, or detect any rhythm in user's movement. If a user is moving with rhythm then this can be used as an input to classify the level of engagement of a person with the user.

For ECG, the heart rate may help classify a person's emotion.

GENERAL

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

Figure 9:
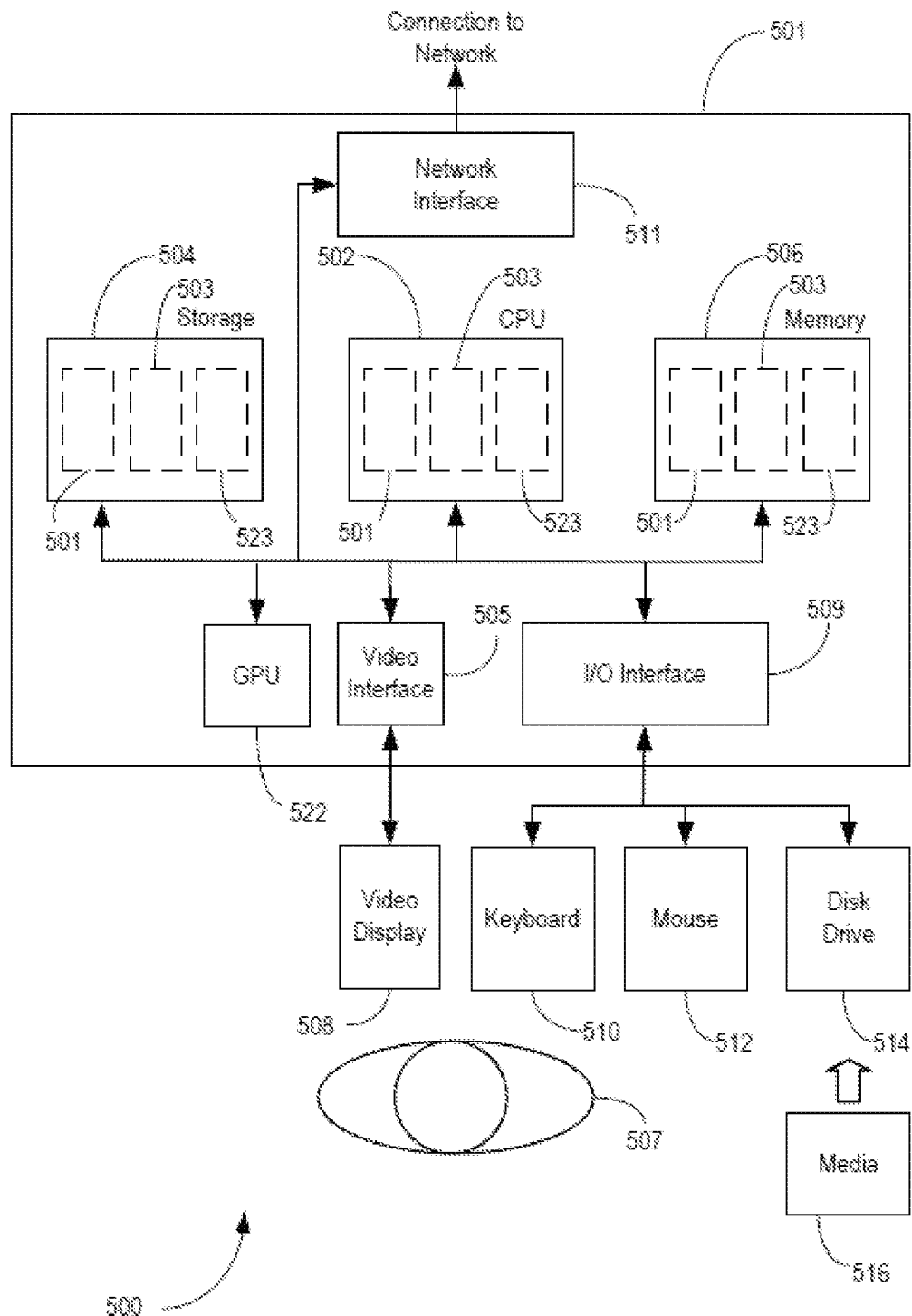
FIG. 9 illustrates a generic computer used to implement aspects of the embodiments described herein.

The present system and method may be practiced in various embodiments. A suitably configured computer device, and associated communications networks, devices, software and firmware may provide a platform for enabling one or more embodiments as described above. By way of example, FIG. 9 shows a generic computer device 500 that may include a central processing unit ("CPU") 502 connected to a storage unit 504 and to a random access memory 506. The CPU 502 may process an operating system 501, application program 503, and data 523. The operating system 501, application program 503, and data 523 may be stored in storage unit 504 and loaded into memory 506, as may be required. Computer device 500 may further include a graphics processing unit (GPU) 522 which is operatively connected to CPU 502 and to memory 506 to offload intensive image processing calculations from CPU 502 and run these calculations in parallel with CPU 502. An operator 507 may interact with the computer device 500 using a video display 508 connected by a video interface 505, and various input/output devices such as a keyboard 510, mouse 512, and disk drive or solid state drive 514 connected by an I/O interface 509. In known manner, the mouse 512 may be configured to control movement of a cursor in the video display 508, and to operate various graphical user interface (GUI) controls appearing in the video display 508 with a mouse button. The disk drive or solid state drive 514 may be configured to accept computer readable media 516. The computer device 500 may form part of a network via a network interface 511, allowing the computer device 500 to communicate with other suitably configured data processing systems (not shown).

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A music system comprising:
   (a) at least one bio-signal sensor configured to capture bio-signal sensor data from at least one user;
   (b) an input receiver configured to receive music data and the bio-signal sensor data, the music data and the bio-signal sensor data being temporally defined such that the music data corresponds temporally to at least a portion of the bio-signal sensor data;
   (c) at least one processor configured to provide:
      (i) a music processor to segment the music data into a plurality of time epochs of music, each epoch of music linked to a time stamp;
      (ii) a sonic feature extractor to, for each epoch of music, extract a set of sonic features;
      (iii) a biological feature extractor to extract, for each epoch of music, a set of biological features from the bio-signal sensor data using the time stamp for the respective epoch of music;

(iv) a metadata extractor to extract metadata from the music data;

(v) a user feature extractor to extract a set of user attributes from the music data and the bio-signal sensor data;

(vi) a machine learning engine to transform the set of sonic features, the set of biological features, the set of metadata, and the set of user attributes into, for each epoch of music, a set of categories that the respective epoch belongs to using one or more predictive models to predict a user reaction to music; and (d) a music recommendation engine configured to provide at least one music recommendation based on the sets of categories;

wherein the music processor is configured to identify a selection of songs from the music data and add a temporal history to the selection of songs, the temporal history indicating a date and time a user of the at least one users listened to or otherwise selected songs of the selection of songs and an order of the selection of songs, wherein the predictive models use a temporal model for the temporal history the selection of songs.

2. The music system of claim 1 wherein the input receiver is configured to receive a target emotional state and wherein the system further comprises a music controller to interact with the music recommendation engine to provide at least one music recommendation based on the target emotional state.

3. The music system of claim 1 wherein the selection of songs provides at least a portion of the metadata used for the recommendation.

4. The music system of claim 1 wherein the at least one processor is configured to provide the one or more predictive models has a learning mode and an operational mode.

5. The music system of claim 1 wherein each of the categories are nested in a hierarchy of nodes or an ordered list of probabilities of the respective category.

6. The music system of claim 1 further comprising a plurality of bio-signal sensors configured to capture bio-signal sensor data from a plurality of users and correlate a portion of the bio-signal sensor data across the plurality of users, the portion being mapped to one or more epochs of music, wherein the machine learning engine transform the portion of the bio-signal sensor data across the plurality of users to a common set of categories for use in music recommendations.

7. The music system of claim 1 further comprising a music effect controller to influence user state by playback or recording of music based the at least one music recommendation.

8. The music system of claim 1 wherein the machine learning engine is to further transform a set of user actions taken during playback of the music data into a set of categories.

9. The music system of claim 8, wherein the set of user actions includes at least one of a volume adjustment, an equalizer adjustment, a song selection, a song skip, a creation of a playlist, and a shuffle of songs.

10. The music system of claim 1 wherein the input receiver includes a microphone to receive music data.

11. The music system of claim 10 wherein the microphone is to detect ambient sounds in a surrounding environment and associated changes in the ambient sounds.

12. The music system of claim 11 wherein the at least one user is a plurality of users, and each of the plurality of users is exposed to the same ambient sounds concurrently.

13. The music system of claim 12 wherein the music recommendation engine is configured to provide a music recommendation for each of the plurality of users.

14. The music system of claim 1 wherein the at least one user is a plurality of users, the music data includes instances of a music track associated with each of the plurality of users, each instance of the music track having standardized tags, and the plurality of time epochs of music for each instance are identified based at least in part on the standardized tags.

15. The music system of claim 14 wherein the standardized tags are universal time-stamps across all instances of the music track.

16. The music system of claim 1 wherein the at least one user is a plurality of users, and each of the plurality of users listens to a music track concurrently.

17. The music system of claim 16 wherein one or more of the plurality of users are locally located to each other.

18. The music system of claim 16 wherein one or more of the plurality of users are remotely located from each other.

19. The music system of claim 16 wherein the music recommendation engine is configured to provide a music recommendation for each of the plurality of users.

* * * * *